United States Patent
Carne et al.

(10) Patent No.: US 9,782,167 B1
(45) Date of Patent: Oct. 10, 2017

(54) BUTTON ACTUATED NEEDLE LOADER

(71) Applicant: Ethicon Endo-Surgery, Inc., Cincinnati, OH (US)

(72) Inventors: Natalie R. Carne, Cincinnati, OH (US); John E. Michael, Lexington, KY (US); Benjamin D. Dickerson, Cincinnati, OH (US); David T. Martin, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 319 days.

(21) Appl. No.: 13/792,976

(22) Filed: Mar. 11, 2013

(51) Int. Cl.
*A61B 17/04* (2006.01)
*A61B 17/06* (2006.01)

(52) U.S. Cl.
CPC .... *A61B 17/0491* (2013.01); *A61B 17/06061* (2013.01); *A61B 17/06114* (2013.01); *A61B 2017/0479* (2013.01)

(58) Field of Classification Search
CPC .......... A61B 2017/0479; A61B 17/062; A61B 17/06061; A61B 17/0479; A61B 17/06114
See application file for complete search history.

(56) References Cited

U.S. PATENT DOCUMENTS

| | | | |
|---|---|---|---|
| 5,437,681 A | 8/1995 | Meade et al. | |
| 5,478,344 A * | 12/1995 | Stone et al. | 606/144 |
| 5,540,704 A * | 7/1996 | Gordon et al. | 606/144 |
| 5,540,706 A | 7/1996 | Aust et al. | |
| 5,674,229 A * | 10/1997 | Tovey et al. | 606/139 |
| 5,792,135 A | 8/1998 | Madhani et al. | |
| 5,817,084 A | 10/1998 | Jensen | |
| 5,846,254 A * | 12/1998 | Schulze et al. | 606/148 |
| 5,878,193 A | 3/1999 | Wang et al. | |
| 6,056,771 A | 5/2000 | Proto | |
| 6,071,289 A | 6/2000 | Stefanchik et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,923,819 B2 | 8/2005 | Meade et al. | |
| 7,524,320 B2 | 4/2009 | Tierney et al. | |
| 7,628,796 B2 | 12/2009 | Shelton, IV et al. | |
| 7,691,098 B2 | 4/2010 | Wallace et al. | |
| 7,806,891 B2 | 10/2010 | Nowlin et al. | |
| 7,824,401 B2 | 11/2010 | Manzo et al. | |

(Continued)

OTHER PUBLICATIONS

U.S. Appl. No. 61/355,832, filed Jun. 17, 2010.
U.S. Appl. No. 61/413,680, filed Nov. 15, 2010.

*Primary Examiner* — Katherine M Shi
*Assistant Examiner* — Michael Mendoza
(74) *Attorney, Agent, or Firm* — Frost Brown Todd LLC

(57) ABSTRACT

An apparatus for loading suture needles into a surgical instrument comprises a body, a drive member, a needle, and a button. The body has a channel configured to receive a surgical instrument. The drive member is configured to open a cover of a surgical instrument upon insertion of a surgical instrument into a channel of the body. The button is configured to deliver the suture needle to a surgical instrument after a surgical instrument has been inserted into the channel and the cover has been opened. The apparatus may further comprise a plate member configured to either prevent downward movement of the button before insertion of a surgical instrument, or participate in the delivery of the needle to a surgical instrument.

14 Claims, 30 Drawing Sheets

(56) References Cited

U.S. PATENT DOCUMENTS

| | | |
|---|---|---|
| 7,862,572 B2 | 1/2011 | Meade et al. |
| 7,976,555 B2 | 7/2011 | Meade et al. |
| 2010/0100125 A1 | 4/2010 | Mahadevan |
| 2011/0313433 A1 | 12/2011 | Woodard, Jr. et al. |
| 2012/0123471 A1 | 5/2012 | Woodard, Jr. et al. |
| 2012/0150199 A1 | 6/2012 | Woodard, Jr. et al. |
| 2013/0282027 A1 | 10/2013 | Woodard, Jr. et al. |

\* cited by examiner

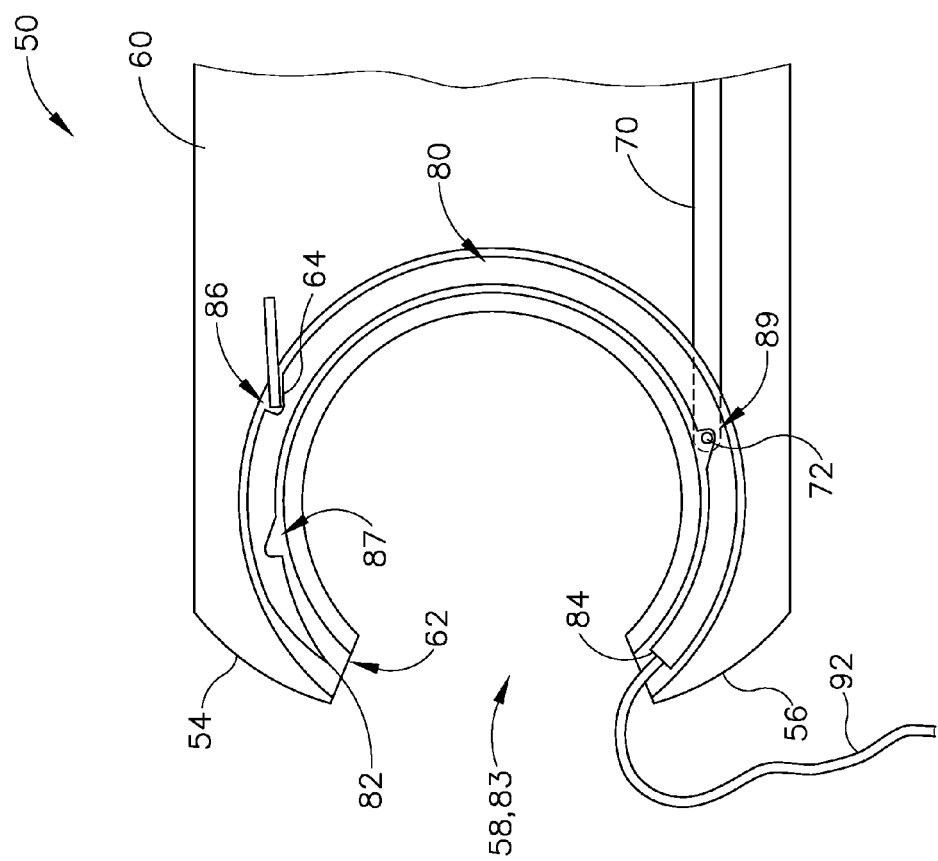

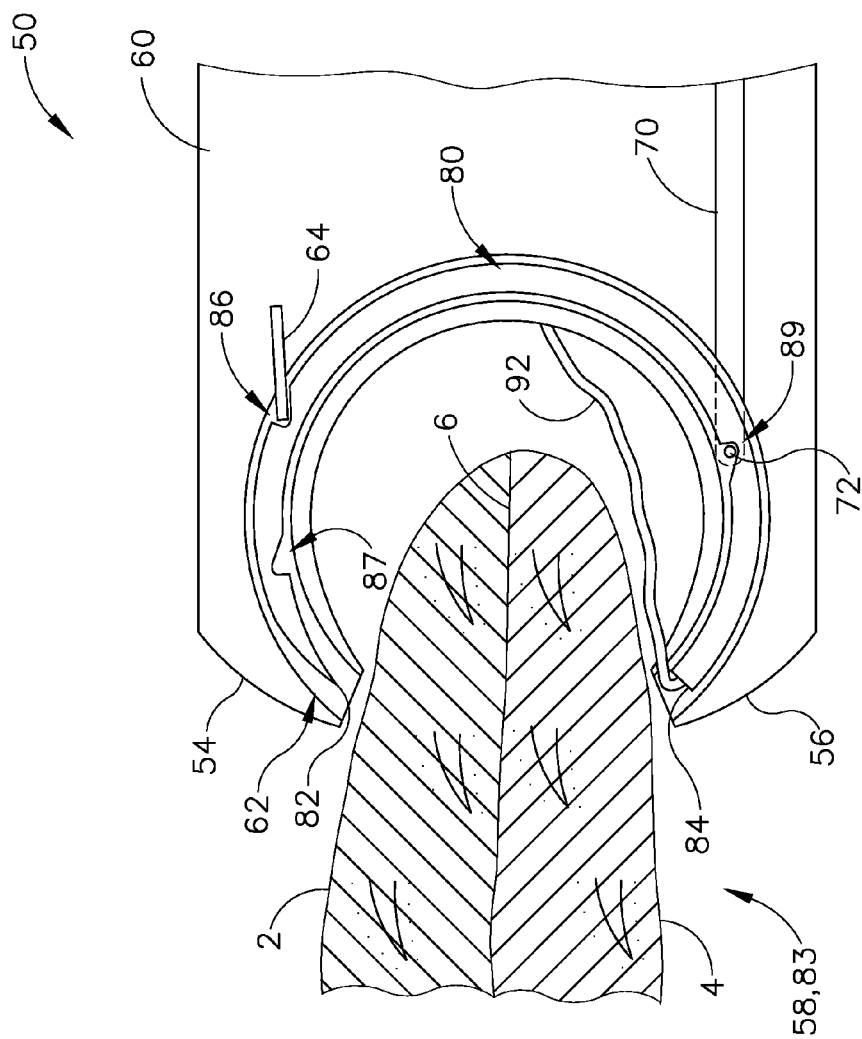

BUTTON ACTUATED NEEDLE LOADER

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio.

Additional suturing instruments are disclosed in U.S. Pat. No. 5,437,681, entitled "Suturing Instrument with Thread Management," issued Aug. 1, 1995, the disclosure of which is incorporated by reference herein; U.S. Pat. No. 5,540,706, entitled "Surgical Instrument," issued Jul. 30, 1996, the disclosure of which is incorporated by reference herein; U.S. Pat. No. 6,923,819, entitled "Apparatus and Method for Surgical Suturing with Thread Management," issued Aug. 2, 2005, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. Pat. No. 7,628,796, entitled "Surgical Suturing Apparatus with Anti-Backup System," issued Dec. 8, 2009, the disclosure of which is incorporated by reference herein; U.S. Pat. No. 7,862,572, entitled "Apparatus and Method for Minimally Invasive Suturing," issued Jan. 4, 2011, the disclosure of which is incorporated by reference herein; U.S. Pat. No. 7,976,555, entitled "Apparatus and Method for Minimally Invasive Suturing," issued Jul. 12, 2011, the disclosure of which is incorporated by reference herein; U.S. Pub. No. 2011/0313433, entitled "Laparoscopic Suture Device with Asynchronous In-Line Needle Movement," filed Jun. 9, 2011, now U.S. Pat. No. 9,168,037, issued on Oct. 27, 2015, the disclosure of which is incorporated by reference herein; U.S. patent application Ser. No. 13/449,494, entitled "Laparoscopic Suturing Instrument with parallel Concentric Shaft Pairs," filed Apr. 18, 2012, now U.S. Pat. No. 9,451,946, issued on Sep. 27, 2016, the disclosure of which is incorporated by reference herein; and U.S. Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; U.S. Pub. No. 2010/0100125, entitled "Suture Needle and Suture Assembly," published Apr. 22, 2010, the disclosure of which is incorporated by reference herein; U.S. Provisional Application Ser. No. 61/413,680, filed Nov. 15, 2010, entitled "Custom Needle for Suture Instrument," the disclosure of which is incorporated by reference herein; U.S. patent application Ser. No. 13/295,186, entitled "Needle for Laparoscopic Suturing Instrument," filed on Nov. 14, 2011, now U.S. Pat. No. 9,125,646, issued on Sep. 8, 2015, the disclosure of which is incorporated by reference herein; and U.S. patent application Ser. No. 13/295,203, entitled "Laparoscopic Suturing Instrument with Dual-Action Needle Graspers," filed on Nov. 14, 2011, now U.S. Pat. No. 8,702,732, issued on Apr. 22, 2014, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5 depicts an enlarged partial elevational view of the needle of FIG. 4 loaded in the end effector of FIG. 2, with a cover of the end effector removed.

FIG. 6A depicts an enlarged partial elevational view of the loaded end effector of FIG. 5, with the end effector positioned about tissue;

Figure 1:
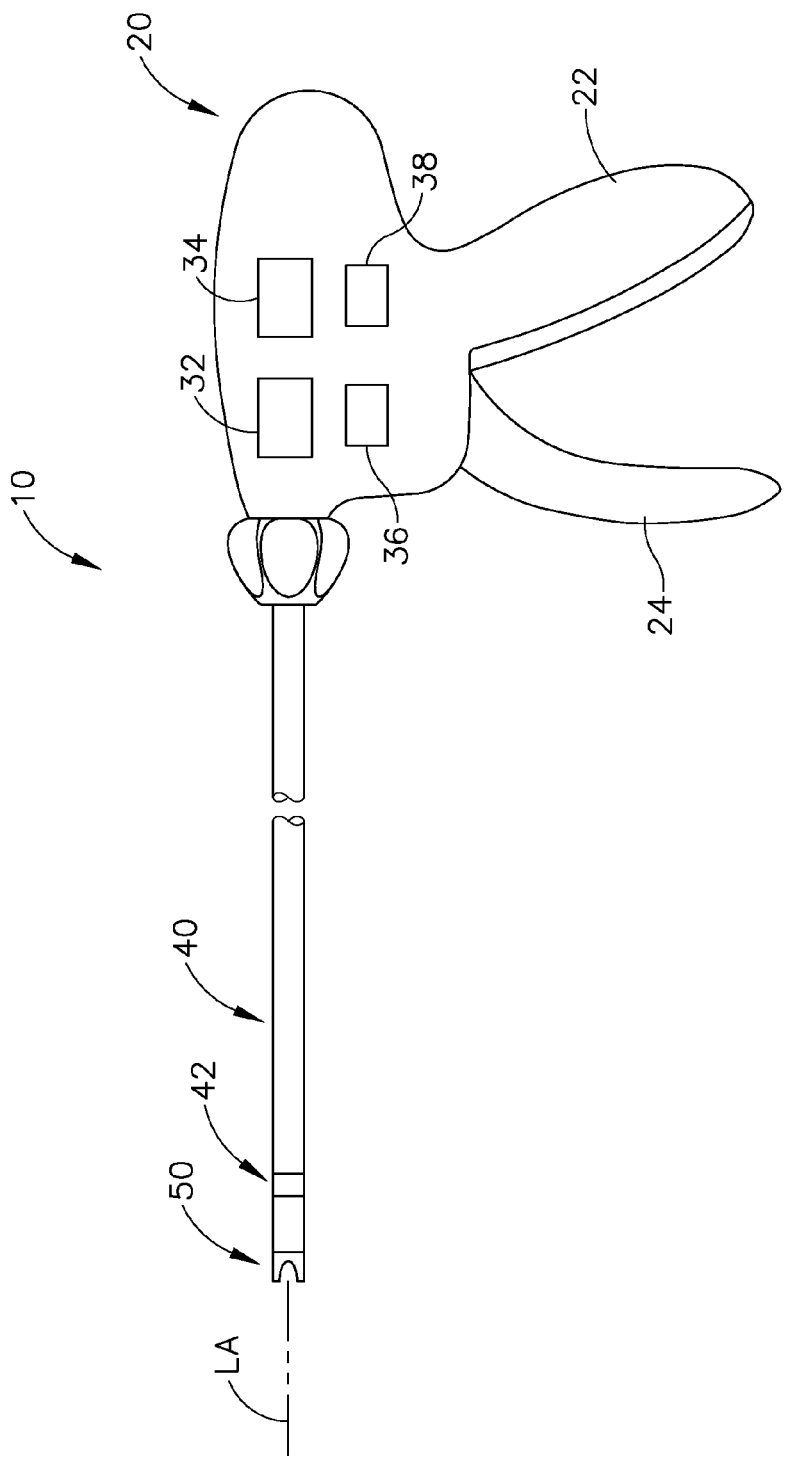
FIG. 1 depicts a schematic elevational view of an exemplary suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Suturing Instrument

FIG. 1 shows an exemplary laparoscopic suturing instrument (10), which may be used to suture tissue in numerous kinds of surgical procedures. Instrument (10) of this example includes a handle portion (20), a shaft (40) extending distally from handle portion (20), and an end effector (50) that is joined to shaft (40) by a joint (42). Handle portion (20) includes a grip (22) and a trigger (24), which is pivotable relative to grip (22) to actuate end effector (50) as will be described in greater detail below. In some versions, shaft (40) and end effector (50) are configured to fit through a conventional trocar. It should therefore be understood that instrument (10) may be used in minimally invasive procedures. Of course, instrument (10) may be used through passageways other than trocars (e.g., through a thoracotomy, etc.) or in open procedures if desired.

In the present example, shaft (40) is rotatable to position end effector (50) at various angular orientations about the longitudinal axis (LA) defined by shaft (40). To that end, handle portion (20) includes a rotation control (32). It should be understood that rotation control (32) may take a variety of forms, including but not limited to a knob, a dial, a grip at the proximal end of shaft (40), etc. Various suitable forms that rotation control (32) may take will be apparent to those of ordinary skill in the art in view of the teachings herein. In addition to providing rotation of end effector (50), instrument (10) also provides articulation of end effector (50). In particular, joint (42) at the distal end of shaft (40) enables end effector (50) to pivotally deflect away from the longitudinal axis (LA) defined by shaft (40) to achieve various articulation angles. It should be understood that these various articulation angles may be achieved at any of the various angular orientations provided through rotation control (32).

Handle portion (20) further includes an articulation control (34), which may include any suitable component such as a knob, a dial, a lever, a slider, etc. Various suitable forms that articulation control (34) may take will be apparent to those of ordinary skill in the art in view of the teachings herein. Similarly, various suitable components and configurations that may be used to provide articulation of end effector (50) at joint (42) in response to actuation of articulation control (34) will be apparent to those of ordinary skill in the art in view of the teachings herein. By way of example only, articulation may be provided in accordance with at least some of the teachings of U.S. Pat. No. 7,862,572, the disclosure of which is incorporated by reference herein.

In some versions, handle portion (20) includes a powered motive source (36). Powered motive source (36) may comprise a motor, a solenoid, and/or any other suitable type of powered motive source. Powered motive source (36) may be used to drive end effector (50) as will be described in greater detail below, to rotate shaft (40), to articulate end effector (50) at joint (42), and/or to provide any other suitable type of operation. It should also be understood that handle portion (20) may include an integral power source (38). By way of example only, integral power source (38) may comprise a rechargeable battery coupled with powered motive source (36). Alternatively, in versions of instrument (10) where at least one component receives electrical power, such electrical power may be provided by an external source that is coupled with instrument (10) via wire, via inductive coupling, or otherwise. It should be understood that versions of instrument (10) having powered motive source (36) and/or integral power source (38) may have additional associated components, including but not limited to transmission components, clutch components, sensors, a control module, etc. Various suitable components and combinations thereof will be apparent to those of ordinary skill in the art in view of the teachings herein. It should also be understood that instrument (10) may simply lack powered motive source (36) and/or power source (38).

Figure 2:
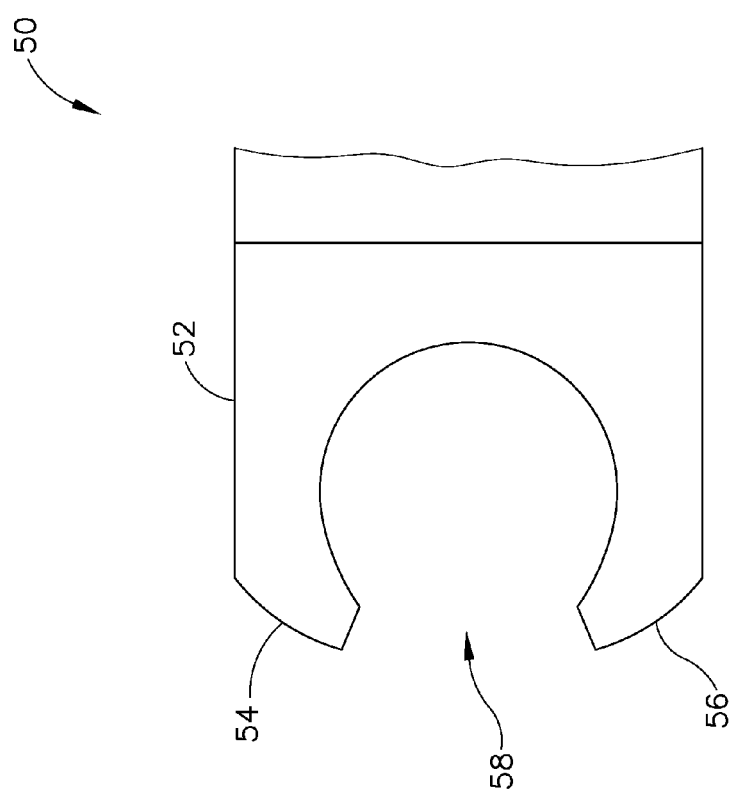
FIG. 2 depicts an enlarged partial elevational view of the end effector of the suturing instrument of FIG. 1.
Figure 3:
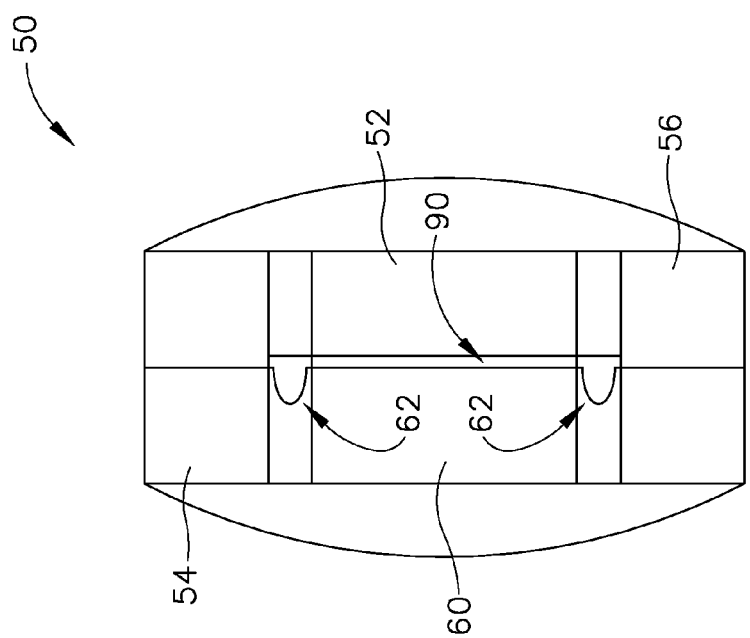
FIG. 3 depicts an end view of the end effector of FIG. 2.

FIGS. 2-3 and 5 show end effector (50) of the present example in greater detail. In particular, end effector (50) of the present example comprises a cover (52), a frame base (60), a needle exit arm (54), and a needle entry arm (56). Arms (54, 56) define a gap (58) for receiving tissue, with end effector (50) being operable to drive a needle (80) with suture (92) through the tissue received in gap (58). Frame base (60) defines a curved channel (62) that terminates at the free end of each arm (54, 56) and that is sized to receive a curved needle (80). Cover (52) is movable relative frame base (60) to selectively cover and uncover channel (62) with needle (80) contained therein. By way of example only, cover (52) may slide proximally relative to frame base (60) to selectively uncover channel (62) and needle (80); and distally relative to frame base (60) to selectively cover channel (62) and needle (80). In some other versions, cover (52) may snap on and off of frame base (60), may pivot toward and away from frame base (60), or be movable in some other fashion. It should also be understood that cover (52) may be movable relative to frame base (60) in accordance with at least some of the teachings of U.S. Pat. No. 7,862,572, the disclosure of which is incorporated by reference herein and/or U.S. Pat. No. 7,976,555, the disclosure of which is incorporated by reference herein. As can be seen in FIG. 3, even when cover (52) is positioned over frame base (60) to cover frame base (60) and needle (80), cover (52) and frame base (60) define a gap (90) that is configured to enable suture (92) to travel through gap (90) as needle (80) is being driven along a circular path as described below, thereby preventing suture (92) from getting stuck in channel (62).

Figure 4:
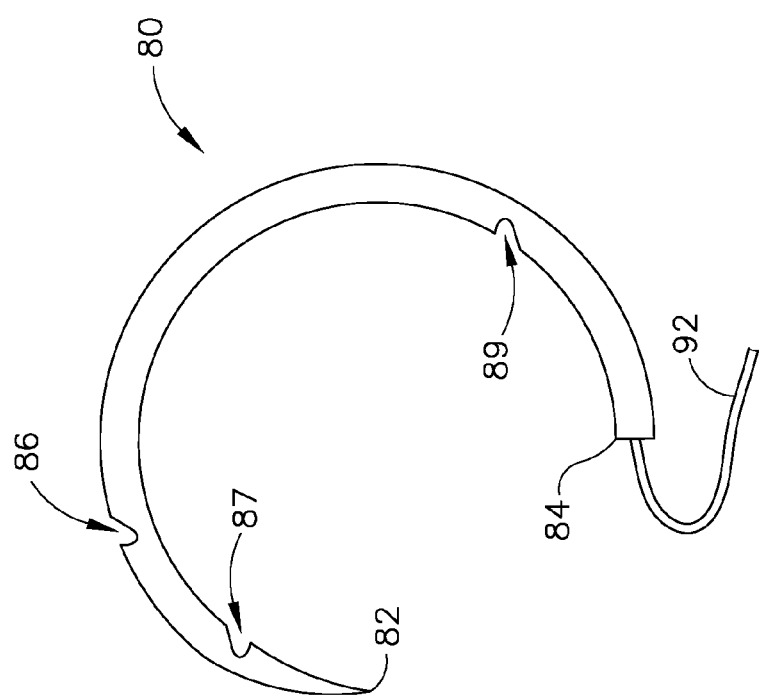
FIG. 4 depicts an elevational view of an exemplary needle suited for use with the suturing instrument of FIG. 1.

As shown in FIG. 4, needle (80) of the present example is curved, forming an incomplete circle. Needle (80) includes a sharp tip (82) and a blunt end (84). In the present example, the body of needle (80) extends along a portion of a circle along approximately 270°, though it should be understood that needle (80) may instead extend through any other suitable angular extent. Sharp tip (82) is configured to pierce tissue repeatedly as needle (80) makes multiple passes through tissue. Suture (92) is integrally secured to the blunt end (84) of needle. Needle (80) is includes an anti-backup notch (86), a needle return notch (87), and a needle drive notch (89). These notches (86, 87, 89) interact with complementary features of end effector (50) as will be described in greater detail below. By way of example only, at least part of needle (80) may be constructed in accordance with at least some of the teachings of U.S. Pub. No. 2012/0123471, entitled "Needle for Laparoscopic Suturing Instrument," published May 17, 2012, now U.S. Pat. No. 9,125,646, issued on Sep. 8, 2015, the disclosure of which is incorporated by reference herein, U.S. Pat. No. 7,862,572, the disclosure of which is incorporated by reference herein and/or U.S. Pat. No. 7,976,555, the disclosure of which is incorporated by reference herein.

As shown in FIG. 5, frame base (60) further includes a pawl (64) and a drive arm (70), which has a drive pin (72). Pawl (64) extends distally and has a free end configured to fit in anti-backup notch (86) of needle (80) when needle (80) is in a home position. Pawl (64) is resiliently biased to extend distally but is further configured to deflect laterally when needle (80) is being driven. By way of example only, pawl (64) may comprise a resilient strip of metal that is integrally secured in frame base (60). As another merely illustrative example, pawl (64) may comprise a rigid member that is pivotally secured to frame base (60) and spring-loaded to provide a resilient bias to the position shown in FIG. 5. Various other suitable configurations for pawl (64) will be apparent to those of ordinary skill in the art in view of the teachings herein. Drive pin (72) is configured to fit in needle return notch (87) and in needle drive notch (89). Drive arm (70) is movable to move pin (72) along a circular path, to thereby drive needle (80) along a circular path. Drive arm (70) may move in response to pivoting of trigger (24) toward grip (22), in response to activation of powered motive source (36), or in response to any other suitable type of input. It should be understood that various types of components and assemblies may be employed to actuate drive arm in response to a user input. By way of example only, such components and assemblies may be constructed in accordance with at least some of the teachings of U.S. Pat. No. 7,862,572, the disclosure of which is incorporated by reference herein. Still other suitable components and assemblies that may be employed to drive drive arm (70) will be apparent to those of ordinary skill in the art in view of the teachings herein.

Figure 6B:
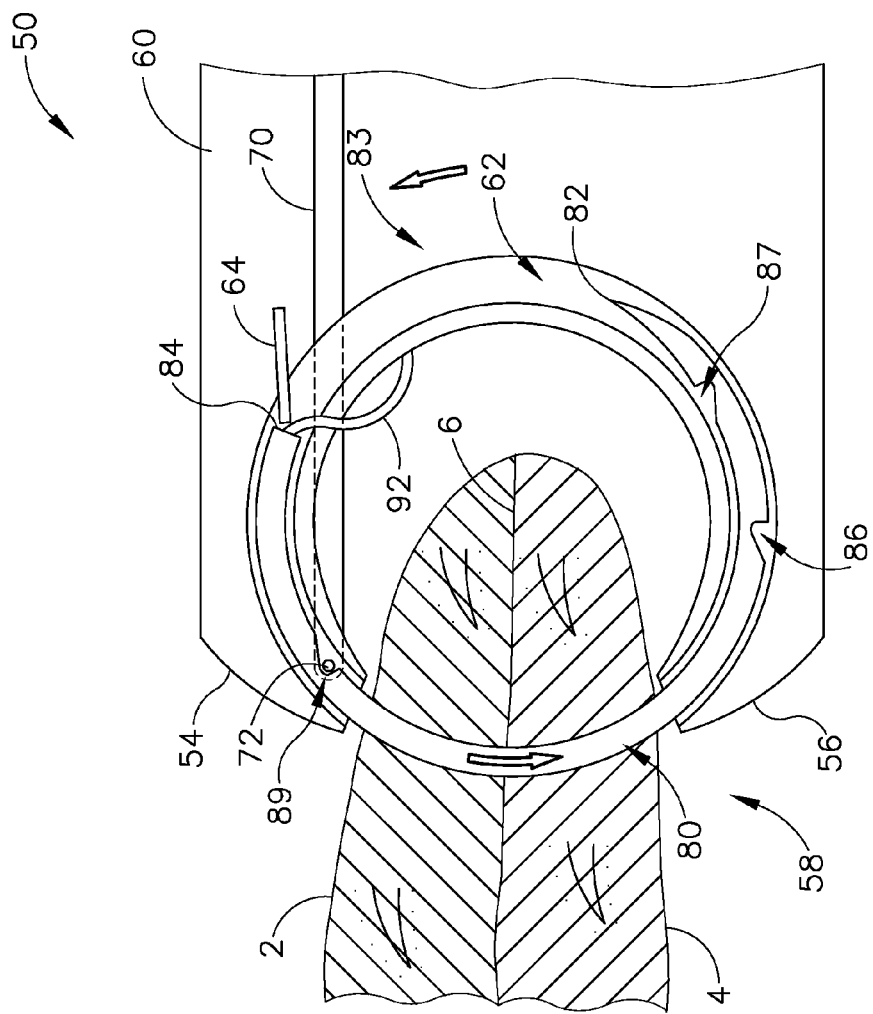
FIG. 6B depicts an enlarged partial elevational view of the loaded end effector of FIG. 5, with the end effector driving the needle through the tissue.

FIGS. 6A-6E show exemplary stages of use of end effector (50) to securely close an incision (6) that splits two layers (2, 4) of tissue. In some uses, end effector (50) is used to simply close an incision (6) that was formed by cutting a single planar layer of tissue with a cutting instrument in a single anatomical structure, with two apposed layers (2, 4) being formed by folding and pinching together the single layer in order to engage end effector (50). In some other uses, end effector (50) is used to suture a layer (2) of tissue of one anatomical structure to a layer (4) of tissue of another anatomical structure. Other suitable contexts for using end effector (50) will be apparent to those of ordinary skill in the art in view of the teachings herein. As shown in FIG. 6A, layers (2, 4) are positioned in gap (58) between arms (54, 56). By way of example only, layers (2, 4) may be manipulated using a set of conventional tissue graspers and/or any other suitable instrumentation to position layers (2, 4) in gap (58). With layers (2, 4) suitably positioned, drive arm (70) is actuated as shown in FIG. 6B to drive needle (80) along a circular path (counterclockwise in the views shown in FIGS. 6A-6E). The orbital motion of arm (70) is transferred to needle (80) via pin (72) in needle drive notch (89). This orbital motion drives needle (80) approximately 180° along a circular path. During this travel, tip (82) pierces both layers (2, 4) of tissue, such that needle (80) is disposed in both layers (2, 4) of tissue.

Figure 6C:
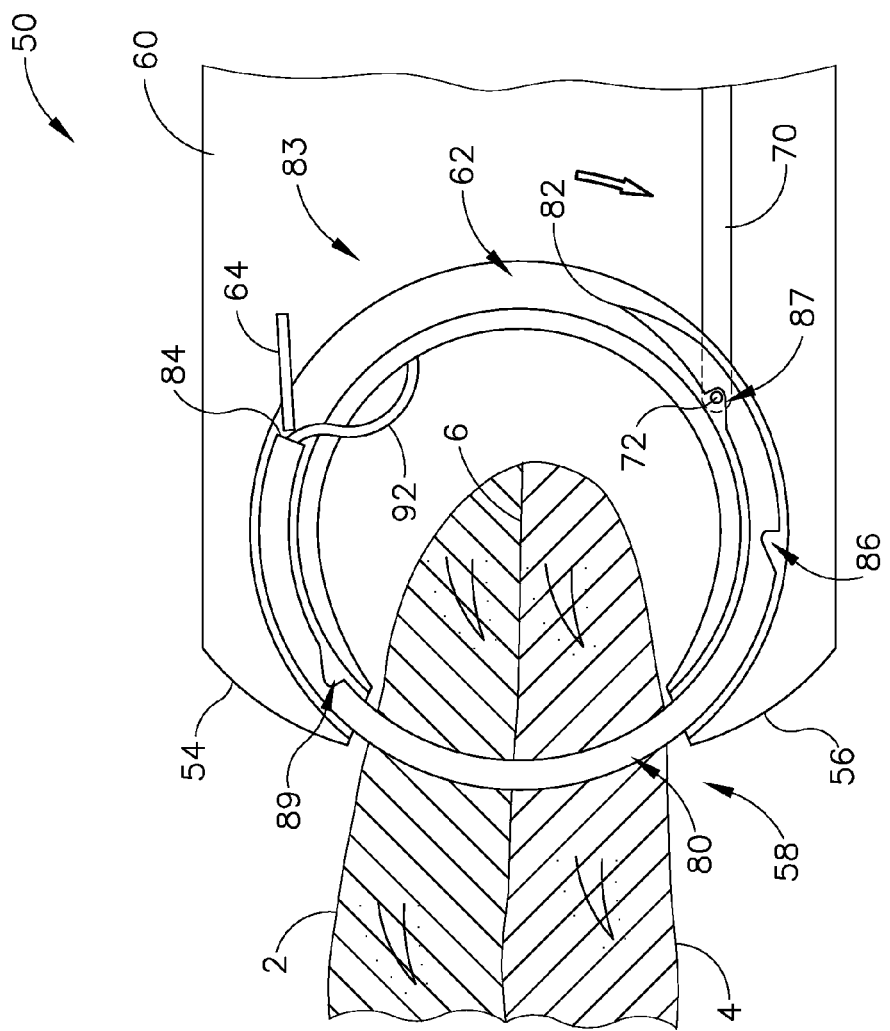
FIG. 6C depicts an enlarged partial elevational view of the loaded end effector of FIG. 5, with the end effector resetting a needle driver.
Figure 6D:
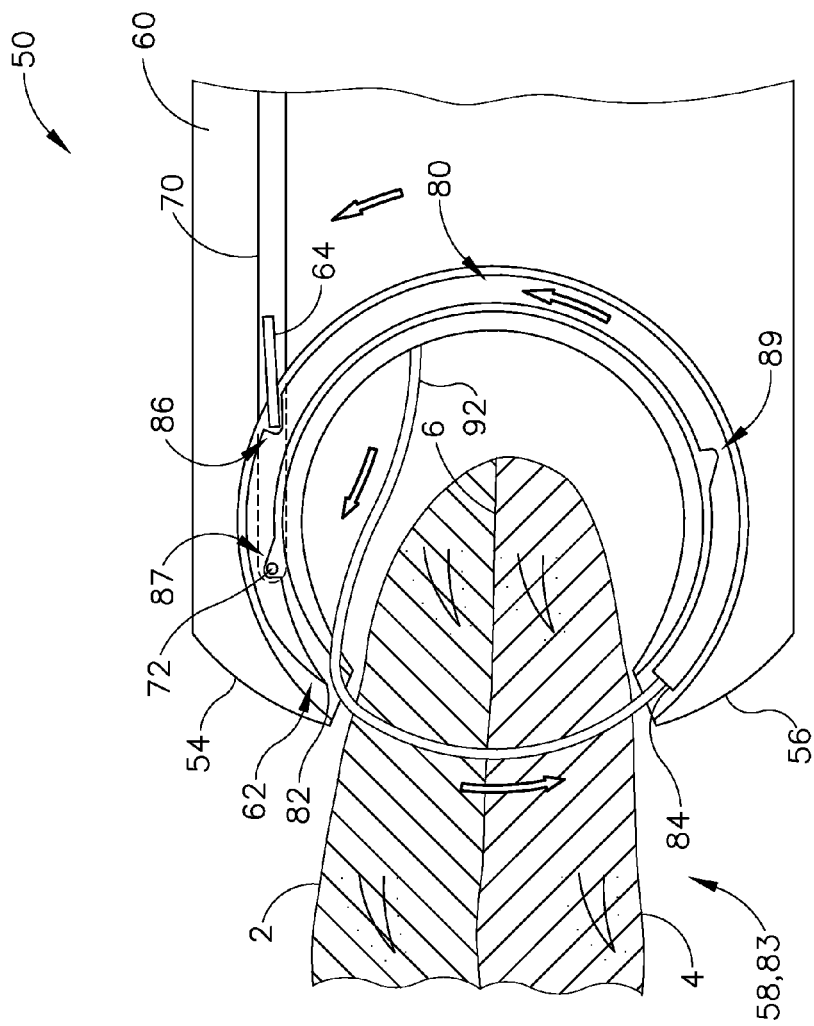
FIG. 6D depicts an enlarged partial elevational view of the loaded end effector of FIG. 5, with the end effector completing a pass of the needle through the tissue, thereby drawing suture through the tissue.

As shown in FIG. 6B, suture (92) has been pulled due to needle (80) being driven along the circular path through channel (62). However, suture (92) does not completely follow needle (80) along the path through channel (62). Instead, suture (92) travels through (90) gap. This allows suture (92) to avoid getting repeatedly wrapped through channel (62) as needle (80) is repeatedly driven through channel (62). As also shown in FIG. 6B, the free end of pawl (64) is positioned behind blunt end (84) of needle (80) at this stage. This prevents needle (80) from traveling in reverse (clockwise in the views shown in FIGS. 6A-6E) as drive arm (70) is returned to the home position as shown in FIG. 6C. When drive arm (70) is driven from the actuated position (FIG. 6B) back to the home position (FIG. 6C), pin (72) pivots away from needle (80) and out of engagement with needle drive notch (89). By way of example only, pin (72) may selectively disengage notch (89) in accordance with at least some of the teachings of U.S. Pat. No. 7,862,572, the disclosure of which is incorporated by reference herein. Still other suitable ways in which pin (72) may selectively disengage notch (89) for return of arm (70) to the home position will be apparent to those of ordinary skill in the art in view of the teachings herein.

With arm (70) to the home position as shown in FIG. 6C, pin (72) is disposed in needle return notch (87). This enables arm (70) to continue driving needle (80) along the circular path, to the position shown in FIG. 6D. In this position, needle (80) has returned to the same home position previously shown in FIG. 6A, such that needle (80) has been completely pulled through both layers (2, 4) of tissue. Needle (80) has thus traveled through a full 360° circular orbital path at this stage, and has thereby completed a full drive stroke. This further results in needle (80) pulling suture (92) through both layers (2, 4) of tissue. Pawl (64) is once again disposed in anti-backup notch (86), again preventing reversal of needle (80). Arm (70) is then again moved back to the home position, with pin (72) disengaging needle return notch (87) in the same manner as the disengagement of pin (72) from needle drive notch (89) as described above.

Figure 6E:
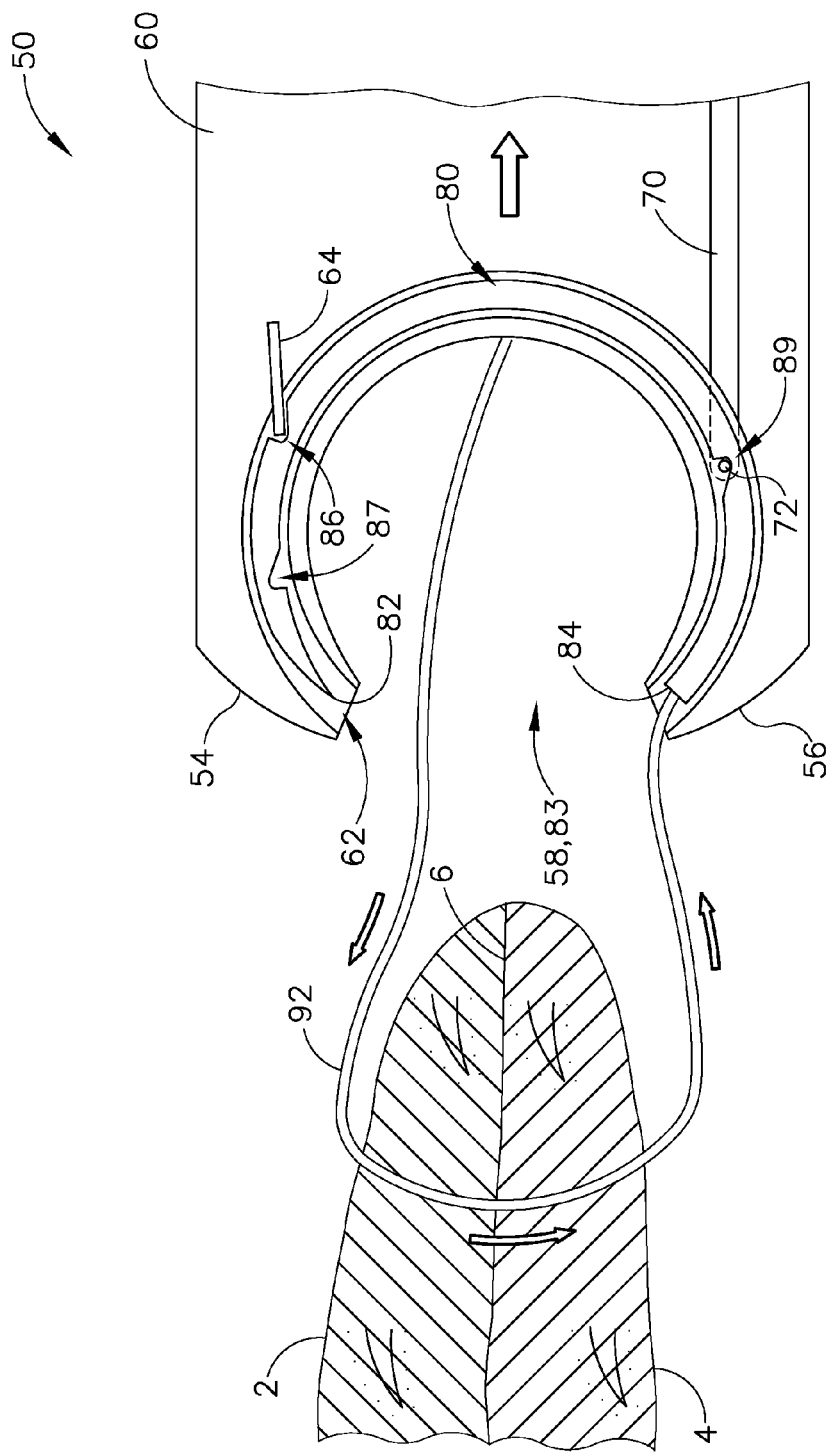
FIG. 6E depicts an enlarged partial elevational view of the loaded end effector of FIG. 5, with the end effector being pulled away from the tissue to pull additional suture through the tissue.
Figure 7:
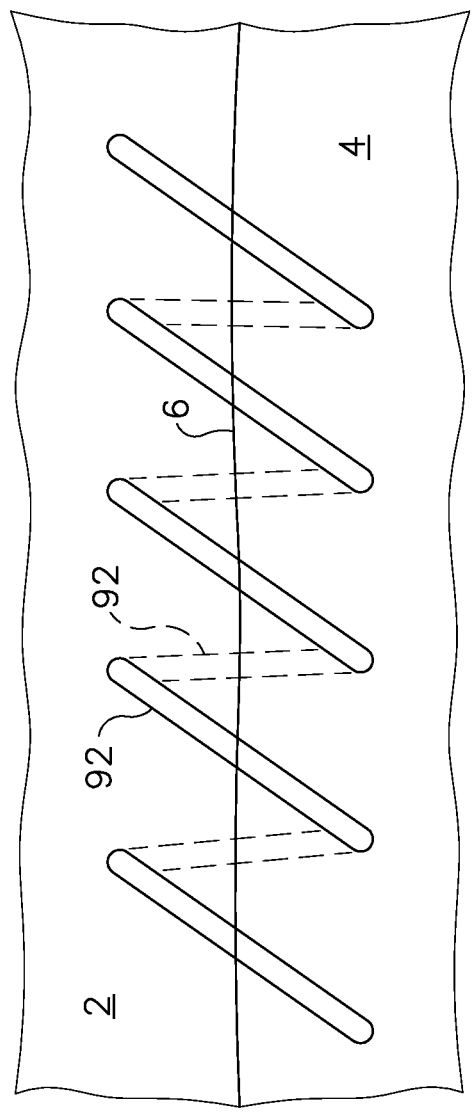
FIG. 7 depicts a top plan view of tissue sutured using the instrument of FIG. 1.

With arm (70) being returned to the home position, the entire end effector (50) is then pulled away from layers (2, 4) of tissue to draw suture (92) through layers (2, 4) of tissue as shown in FIG. 6E. To the extent that this creates tension on suture (92) that might urge needle (80) to back out through channel (62), engagement between pawl (64) and anti-backup notch (86) prevents such backing out of needle (80). After pulling additional length of suture (92) through layers (2, 4) of tissue as shown in FIG. 6E, end effector (50) may be moved to another position along incision (6), with layers (2, 4) being repositioned in gap (58), such that the process shown in FIGS. 6A-6E may be repeated any number of times as desired to create a series of stitches along incision (6). The resulting stitches may appear similar to what is shown in FIG. 7. As shown, the portion of suture (92) disposed within layers (2, 4) of tissue is oriented generally transversely to the line defined by incision (60); while the portion of suture (92) that is external to layers (2, 4) of tissue is oriented obliquely relative to the line defined by incision (60). Of course, suture (92) may instead have any other types of configurations after being passed through layers (2, 4) of tissue to form a series of stitches. Other suitable ways in which instrument (10) may be used will be apparent to those of ordinary skill in the art in view of the teachings herein.

II. Exemplary Needle Loaders

In some instances, it may be necessary for an operator to load a needle (80) in end effector (50). This may be necessary before a suturing procedure begins. This may also be necessary in the middle of a suturing procedure, such that operator may discard a used needle (80) from end effector (50) and replace it with a new needle (80). It may be desirable to make this process fast and easy; and to avoid risks of an operator inadvertently contacting sharp tip (82) while loading needle (80) in end effector. Accordingly, it may be desirable to provide a needle loading cartridge that may receive end effector (50) for substantially automated loading of a needle (80). Various examples of needle loading cartridges will be described in greater detail below; while other examples will be apparent to those of ordinary skill in the art in view of the teachings herein.

A. First Exemplary Button Actuated Needle Loader

Figure 8:
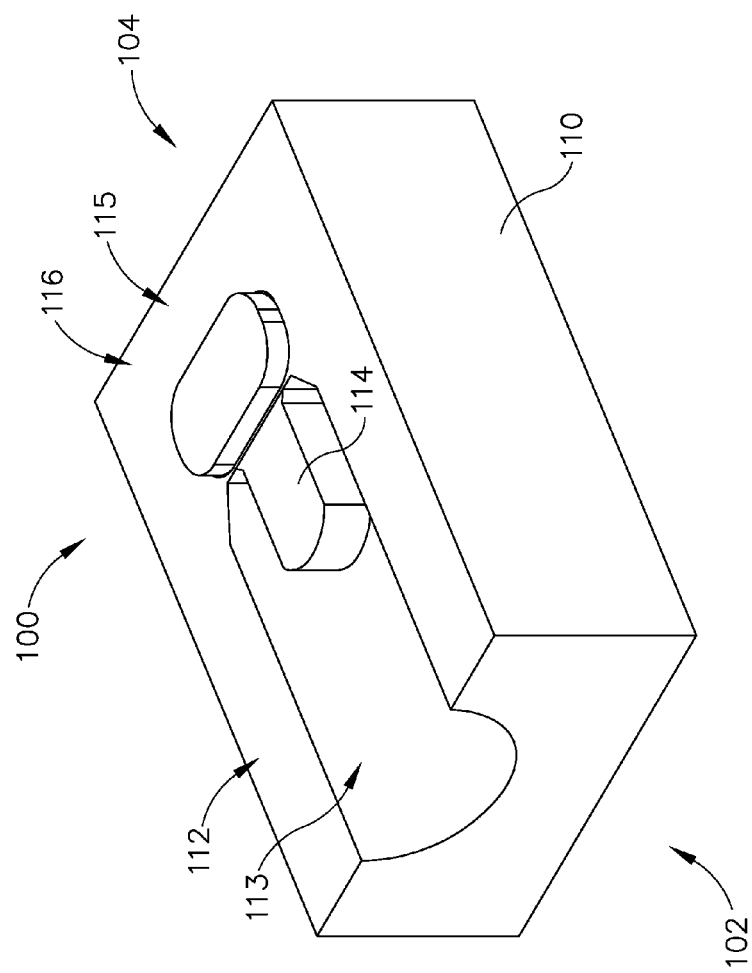
FIG. 8 depicts a perspective view of an exemplary needle loader suitable for use with the instrument of FIG. 1.
Figure 9A:
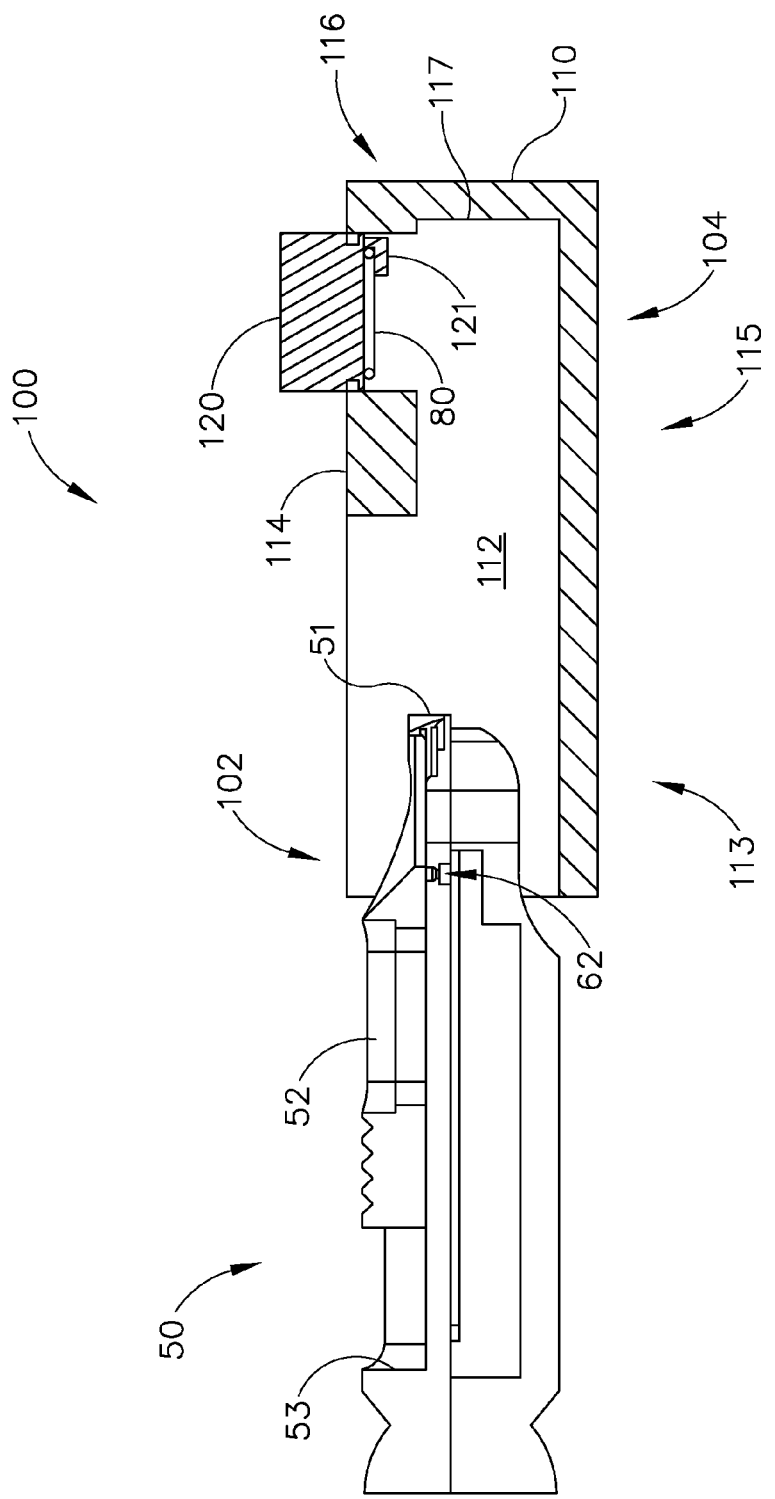
FIG. 9A depicts a side cross sectional view of the suturing instrument of FIG. 1 being inserted into the needle loader of FIG. 8.
Figure 9B:
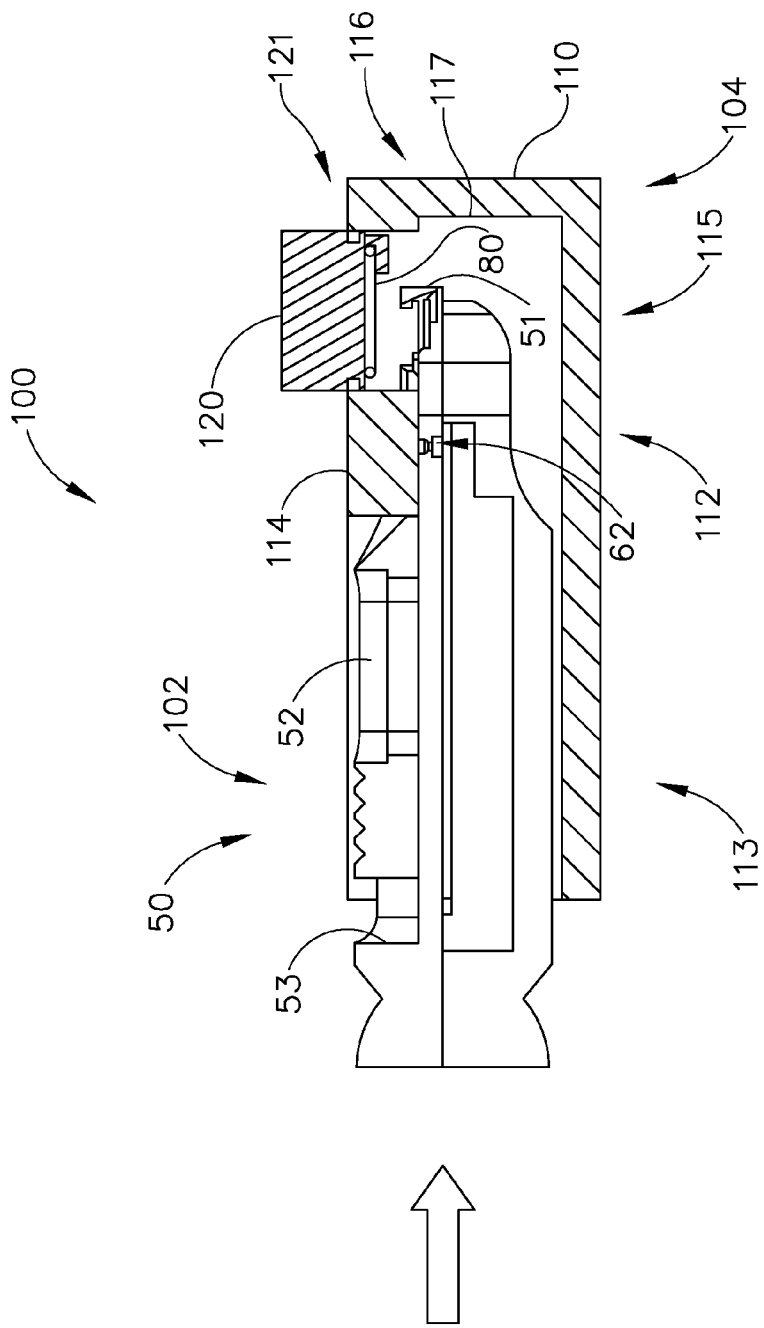
FIG. 9B depicts a side cross sectional view of the suturing instrument of FIG. 1 engaging a drive member of the needle loader of FIG. 8.
Figure 9C:
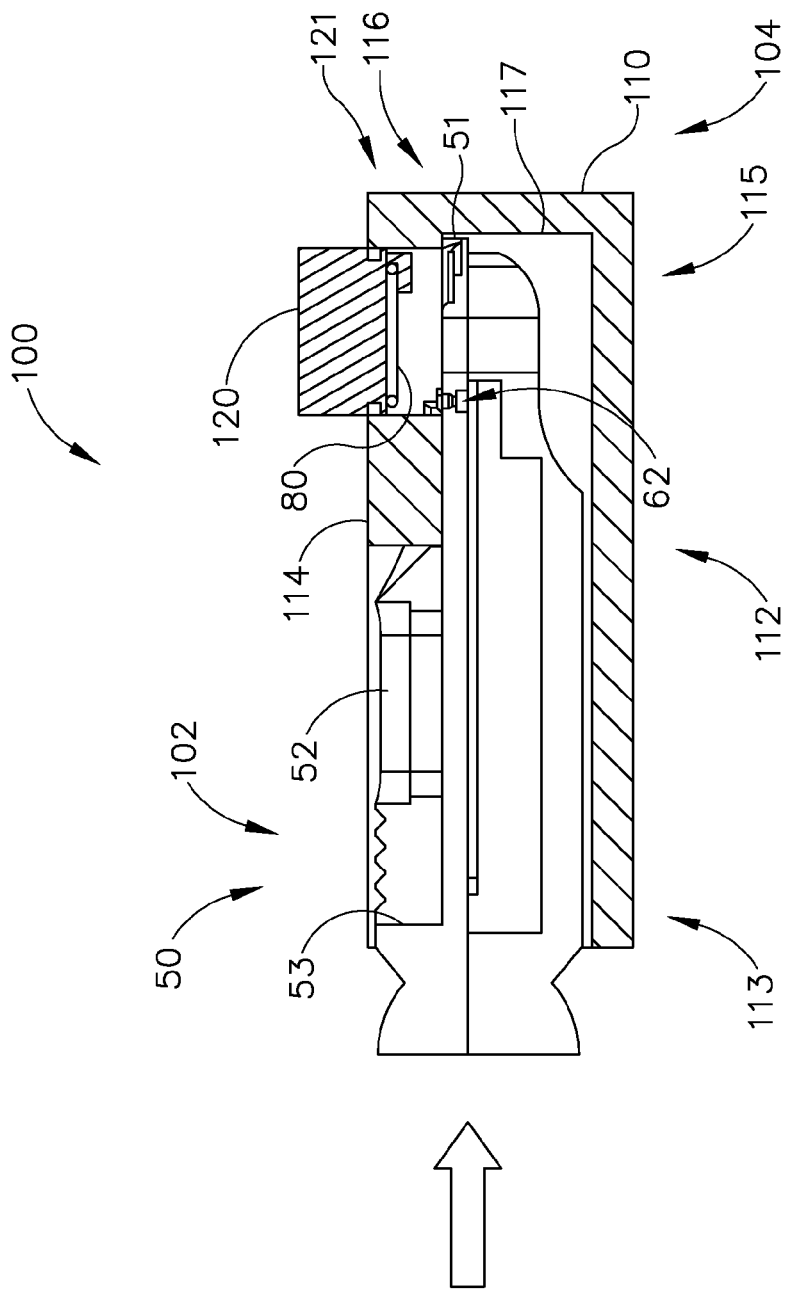
FIG. 9C depicts a side cross sectional view of the suturing instrument of FIG. 1 fully inserted into the needle loader of FIG. 8.
Figure 9D:
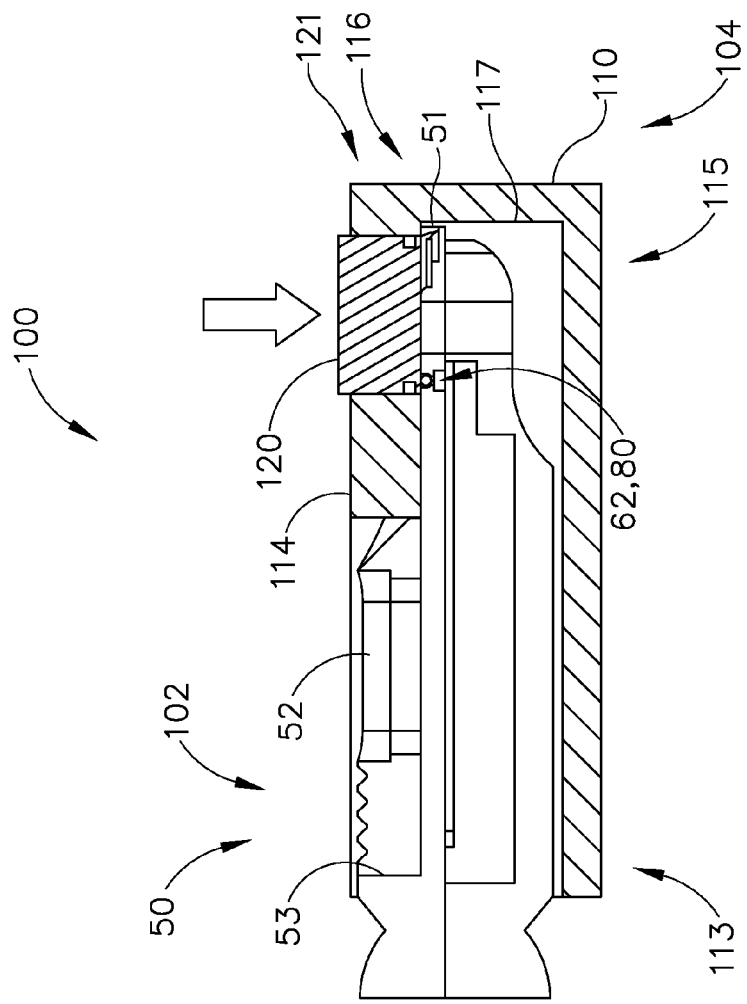
FIG. 9D depicts a side cross sectional view of the suturing instrument of FIG. 1 receiving a needle from the needle loader of FIG. 8.
Figure 9E:
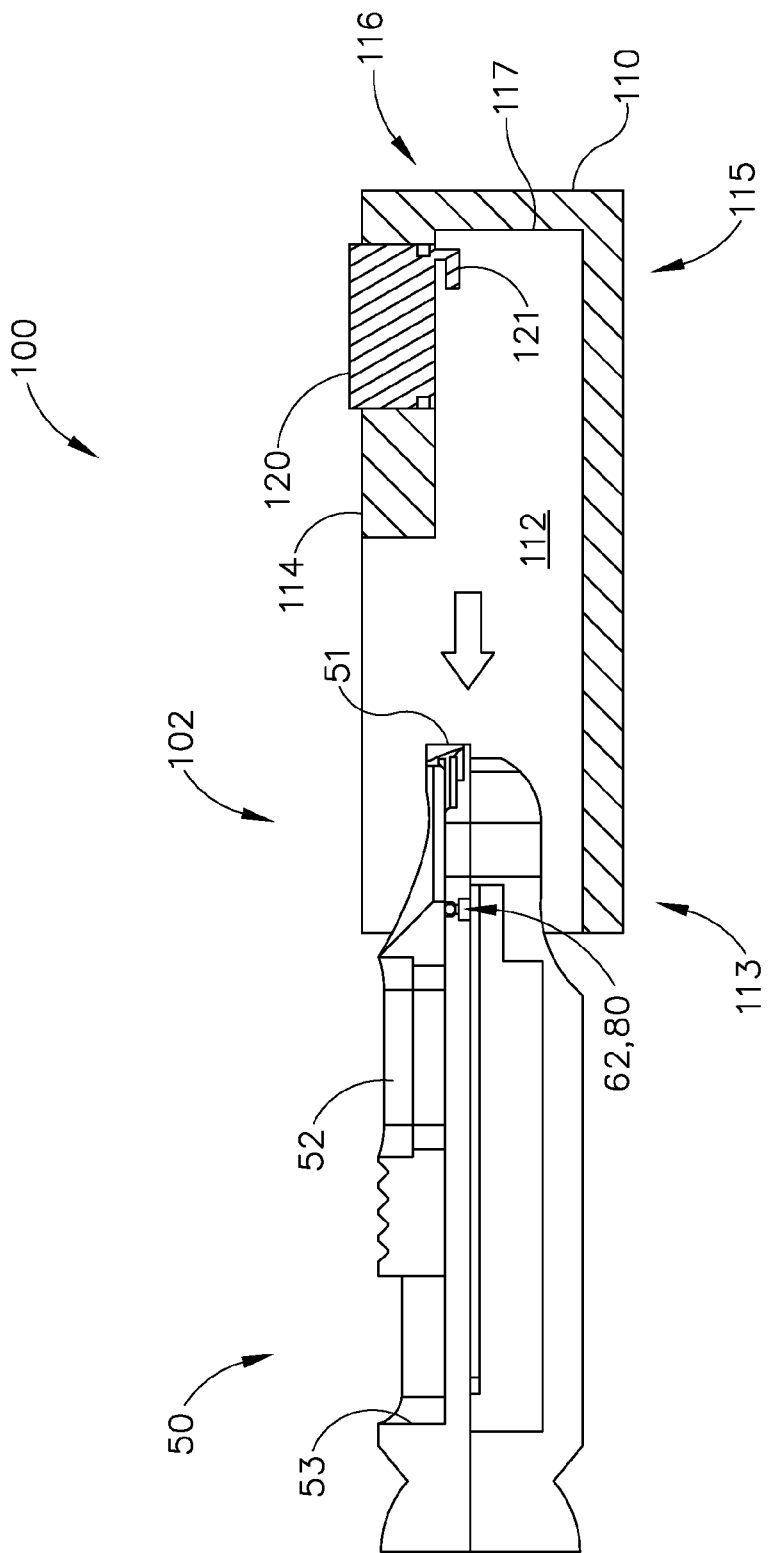
FIG. 9E depicts a side cross sectional view of the suturing instrument of FIG. 1 being removed from the needle loader of FIG. 8.

FIGS. 8-9E show an exemplary needle loader (100) that may be used to load a needle (80) in end effector (50). Needle loader (100) comprises a body (110), a button (120), and needle (80). Body (110) comprises a channel (112) and an engagement member (114). Channel (112) is configured to receive end effector (50) of instrument (10). A proximal portion (113) of channel (112) is uncovered while a distal portion (115) of channel (112) is covered. As best seen in FIG. 8, engagement member (114) protrudes into channel (112) and extends proximally in parallel with an axis defined by channel (112), from distal portion (115) of channel (112) toward proximal portion (113) of channel (112). The width of engagement member (114) is less than the width of channel (112) at the point where engagement feature (114) protrudes into channel (112), such that channel (112) is uncovered on either side of engagement member (114). Body (110) further comprises a transverse opening (116) located at a distal portion (104) of body (110). Opening (116) extends into distal portion (115) of channel (112). Button (120) is slidably disposed within opening (116) of body (110). As seen in FIG. 9A, needle (80) is releasably secured to the bottom of button (120). In the present example, needle (80) is secured to the bottom of button (120) by a needle retainer (121) such that an opening (83) of needle (80) is in a proximal direction; however, various other suitable ways in which needle (80) may be releasably secured to the bottom of button (120) will be apparent to those of ordinary skill in the art in view of the teachings herein. For instance, and by way of example only, the underside of button (120) may be magnetized, may include needle retention tabs, may include needle retention crush ribs, etc. In some versions, button (120) is resiliently biased to the upward position shown in FIGS. 8 and 9A-9C (e.g., by a coil spring, etc.).

In an exemplary use, needle loader (100) is used to insert needle (80) into curved channel (62) of end effector (50). As shown in FIG. 9A, end effector (50) of instrument (10) is inserted into proximal portion (113) of channel (112). End effector (50) is oriented such that cover (52) of end effector (50) is up. As shown in FIG. 9B, end effector (50) is further distally inserted into channel (112) along the longitudinal axis defined by channel (112). During the process of inserting end effector (50) into channel (112), engagement member (114) contacts cover (52) and begins to drive cover (52) in a proximal direction, thereby revealing curved channel (62). As shown in FIG. 9C, after such contact, end effector (50) is further distally inserted into channel (112) along the longitudinal axis defined by channel (112) until a distal end (51) of end effector (50) contacts a distal wall (117) of channel (112) such that end effector (50) cannot be further inserted into channel (112). It should be understood that although the depth of insertion of end effector (50) into channel (112) in this example is controlled by contact between distal end (51) and distal wall (117), the depth of insertion of end effector (50) into channel (112) may alternatively be controlled by contact between cover (52) and a proximal wall (53) of end effector (50). For instance, end effector (50) could be inserted into channel (112) until engagement member (114) drives a proximal end of cover (52) to contact proximal wall (53) such that end effector (50) cannot be further inserted into channel (112). It should also be understood that both contact between distal end (51) and distal wall (117) and contact between cover (52) and a proximal wall (53) may occur simultaneously. Other suitable ways of restricting the depth of insertion of end effector (50) will be apparent to those of ordinary skill in the art in view of the teachings herein.

As shown in FIG. 9C, once end effector (50) is fully inserted into channel (112), cover (52) will have been driven proximally to a proximal location by engagement member (114) such that curved channel (62) is exposed. At this point, the operator presses button (120) downwardly through opening (116) until the bottom of button (120) contacts end effector (50) as shown in FIG. 9D. In this position, needle (80) will be encompassed by curved channel (62). While button (120) is still depressed and needle (80) is still within curved channel (62), end effector (50) is removed from channel (112) distally along the longitudinal axis defined by channel (112). The initial longitudinal movement of end effector (50) removes needle (80) from needle retainer (121) of button (120) such that needle (80) is no longer secured to button (120). As shown in FIG. 9E, as end effector (50) is further removed from channel (112), cover (52) returns to its original position because it is no longer being driven by engagement member (114).

Once end effector (50) is completely removed from needle loader (100), needle (80) should be oriented such that opening (83) of needle (80) aligns with gap (58) of end effector (50) as shown in FIG. 5. After this, instrument (10) is ready for use. It should be noted that needle loader (100) may further comprise suturing thread within body (110), such that the suturing thread is spooled about an internal or external portion of body (110). Such suturing thread may be already secured to needle (80), such that the operator will pull suturing thread from body (110) as the operator pulls the loaded end effector (50) away from body (110). However, body (110) need not comprise suturing thread. By way of example only, suturing thread may be provided as a separate component of needle loader (100).

B. Second Exemplary Button Actuated Needle Loader

Figure 10:
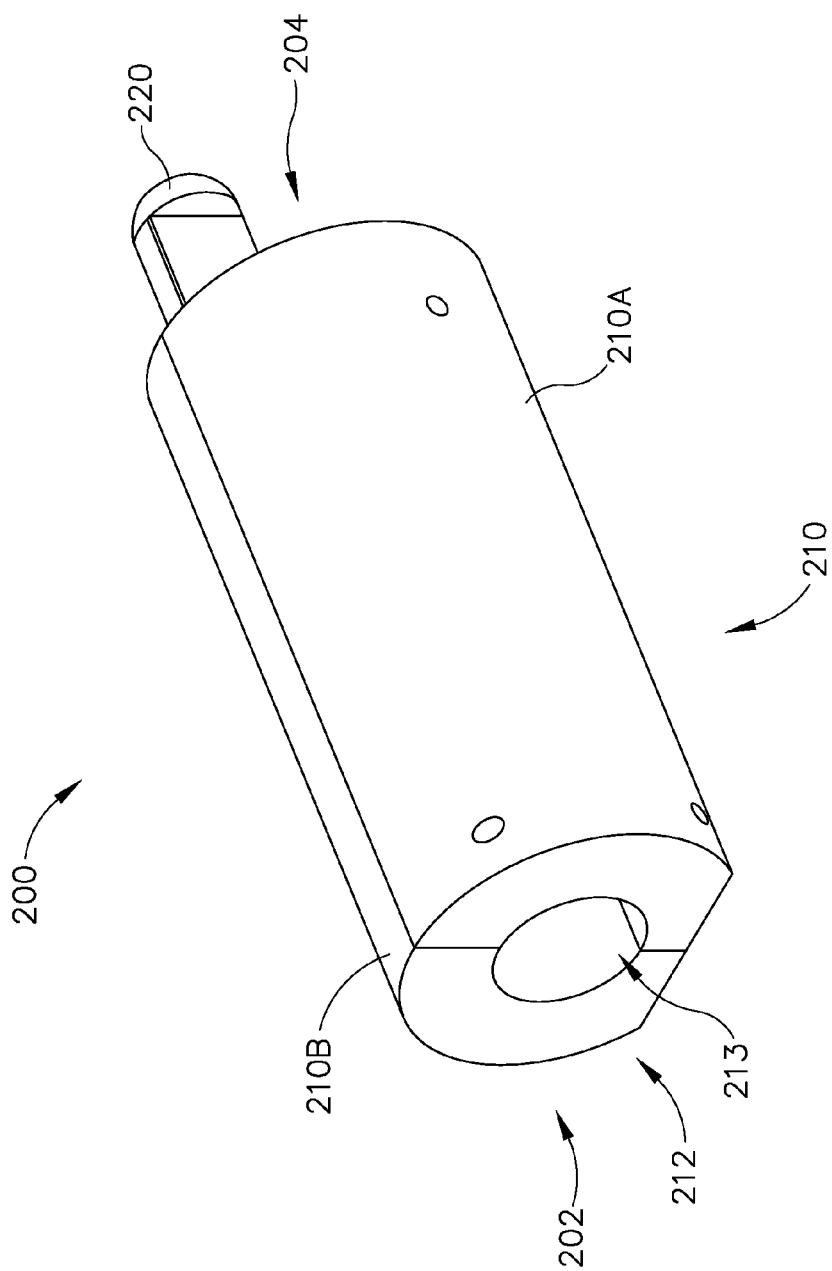
FIG. 10 depicts a perspective view of an exemplary alternative needle loader suitable for use with the instrument of FIG. 1.

FIG. 10 shows another exemplary alternative needle loader (200) that may be used to load a needle (80) in end effector (50). Needle loader (200) of this example comprises a body (210), a button (220), a plate (230), and needle (80). Body (210) comprises a first portion (210A) and a second portion (210B) that together define a first channel (212) and a second channel (216). First channel (212) is configured to receive end effector (50) of instrument (10). Second channel (216) is configured to receive button (220) and plate (230).

Figure 11:
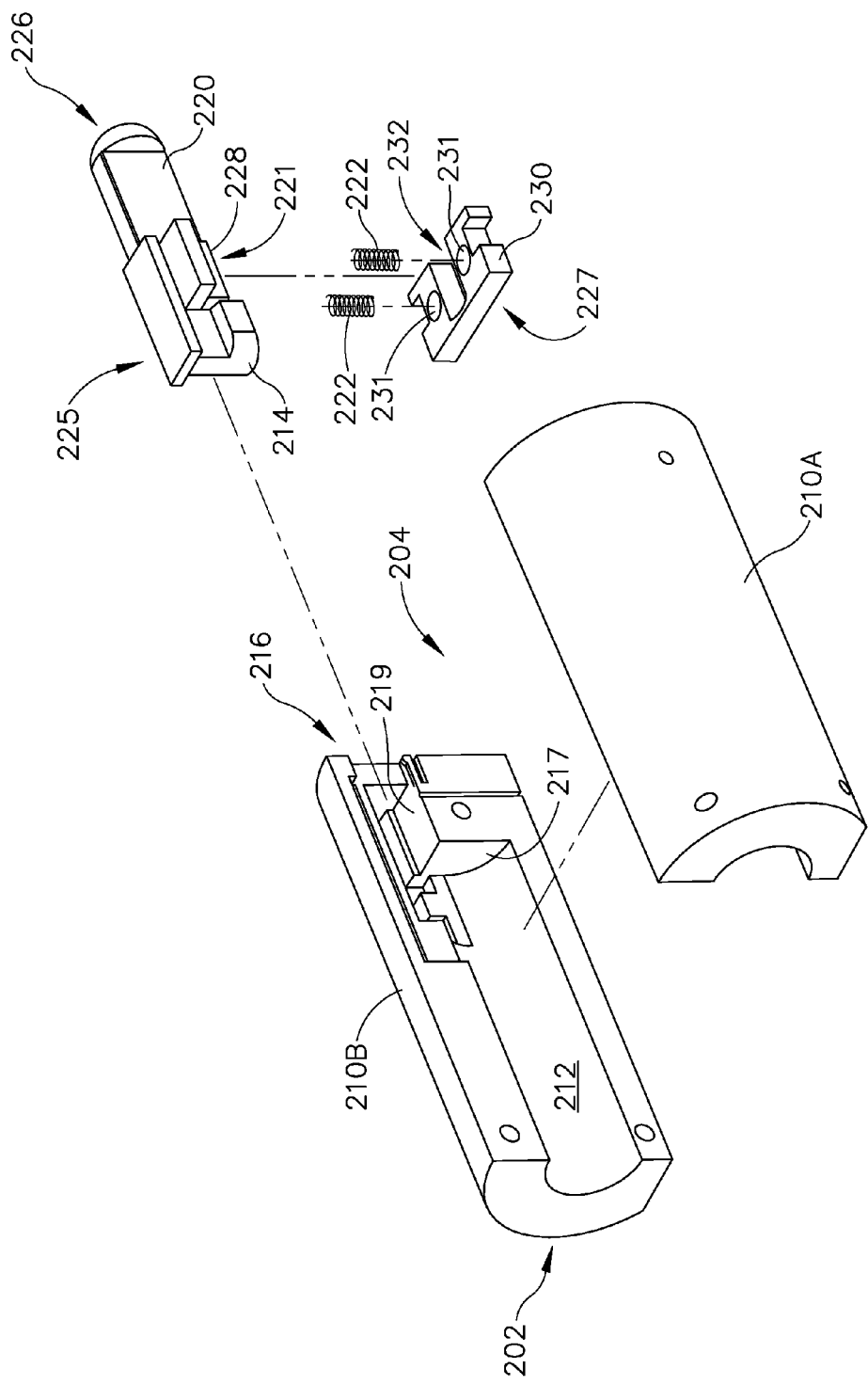
FIG. 11 depicts an exploded perspective view of the needle loader of FIG. 10.
Figure 12A:
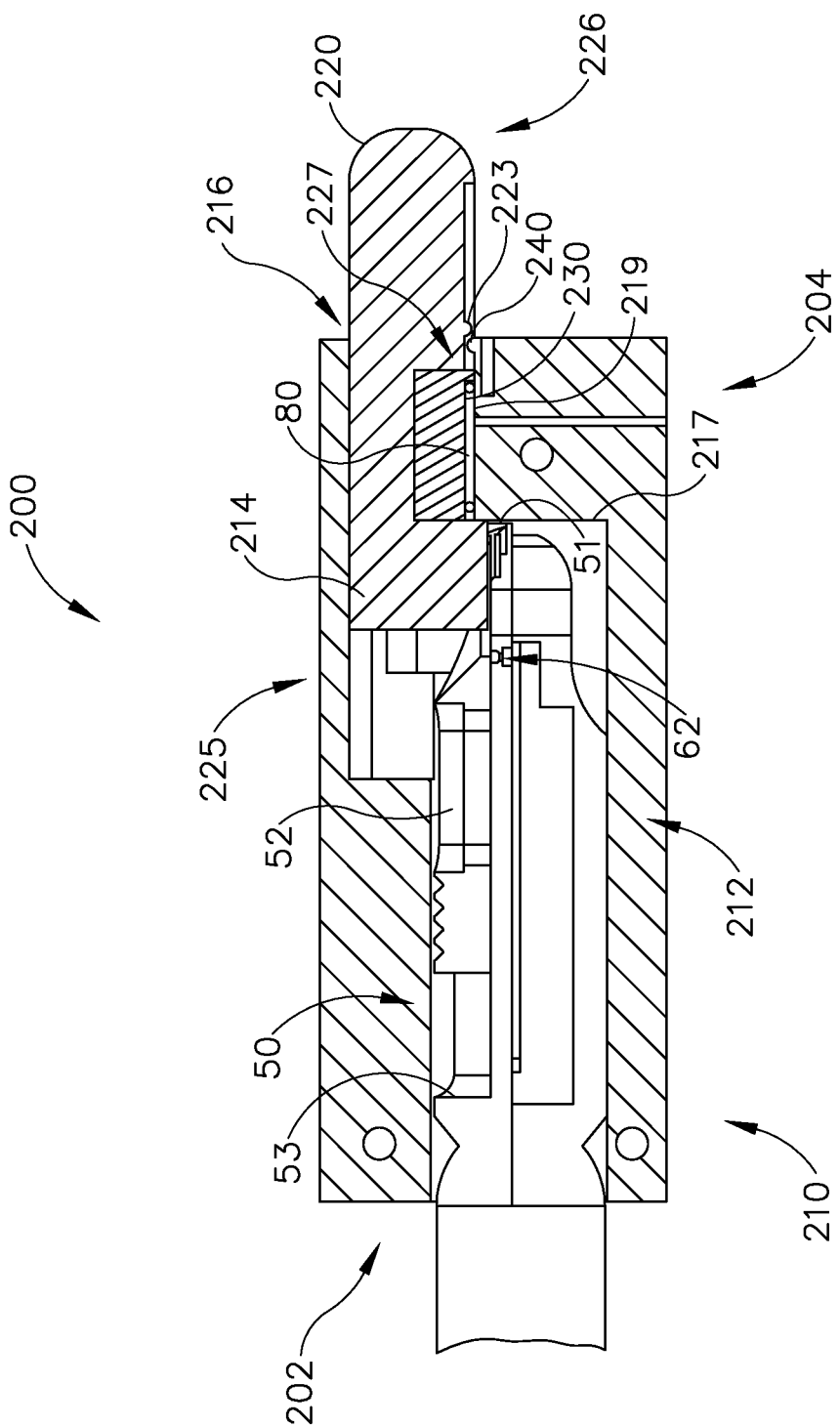
FIG. 12A depicts a side cross sectional view of the suturing instrument of FIG. 1 fully inserted into the needle loader of FIG. 10.

As best seen in FIG. 11, plate (230) comprises a slot (232) that is configured to slidably receive a bottom portion (228) of button (220). Plate (230) further comprises a pair of recesses (231). Button (220) comprises a pair of recesses (221) configured to align with pair of recesses (231) of plate (230). A pair of springs (222) is disposed within recesses (221) and recesses (223) such that an end of each spring (222) is disposed within a respective recess (221) of button (220) and another end is disposed within a corresponding respective recess (223) of plate (230). Springs (222) exert a downward bias upon plate (230). Once assembled, button (220) and plate (230) are slidably disposed within second channel (216), with springs (222) in a compressed state. As best seen in FIG. 12A, a surface (219) of second channel (216) prevents plate (230) from moving downwardly due to the bias exerted upon plate (230) by springs (222). A protrusion (240) is located at the opening of second channel (216). A mating protrusion (223) is located along the bottom surface of button (220). Protrusions (223, 240) prevent button (220) from inadvertently sliding proximally within second channel (216). Needle (80) is releasably secured to the bottom of plate (230). In the present example, needle (80) is secured to the bottom of button (220) by a needle retainer (227) such that opening (83) of needle (80) is in a proximal direction; however, various other suitable ways in which needle (80) may be releasably secured to the bottom of button (220) will be apparent to those of ordinary skill in the art in view of the teachings herein. For instance, and by way of example only, the underside of button (220) may be magnetized, may include needle retention tabs, may include needle retention crush ribs, etc.

Button (220) further comprises an engagement member (214) at a proximal end (225) of button (220). As best seen in FIG. 12A, engagement member (214) protrudes into first channel (212) and extends proximally along an axis defined by first channel (212) from distal portion (215) of first channel (212) toward proximal portion (213) of first channel (212). The width of engagement member (214) is less than the width of first channel (212) at the point where engagement feature (214) protrudes into first channel (212), such that a portion of first channel (212) is on either side of engagement member (214).

Figure 12B:
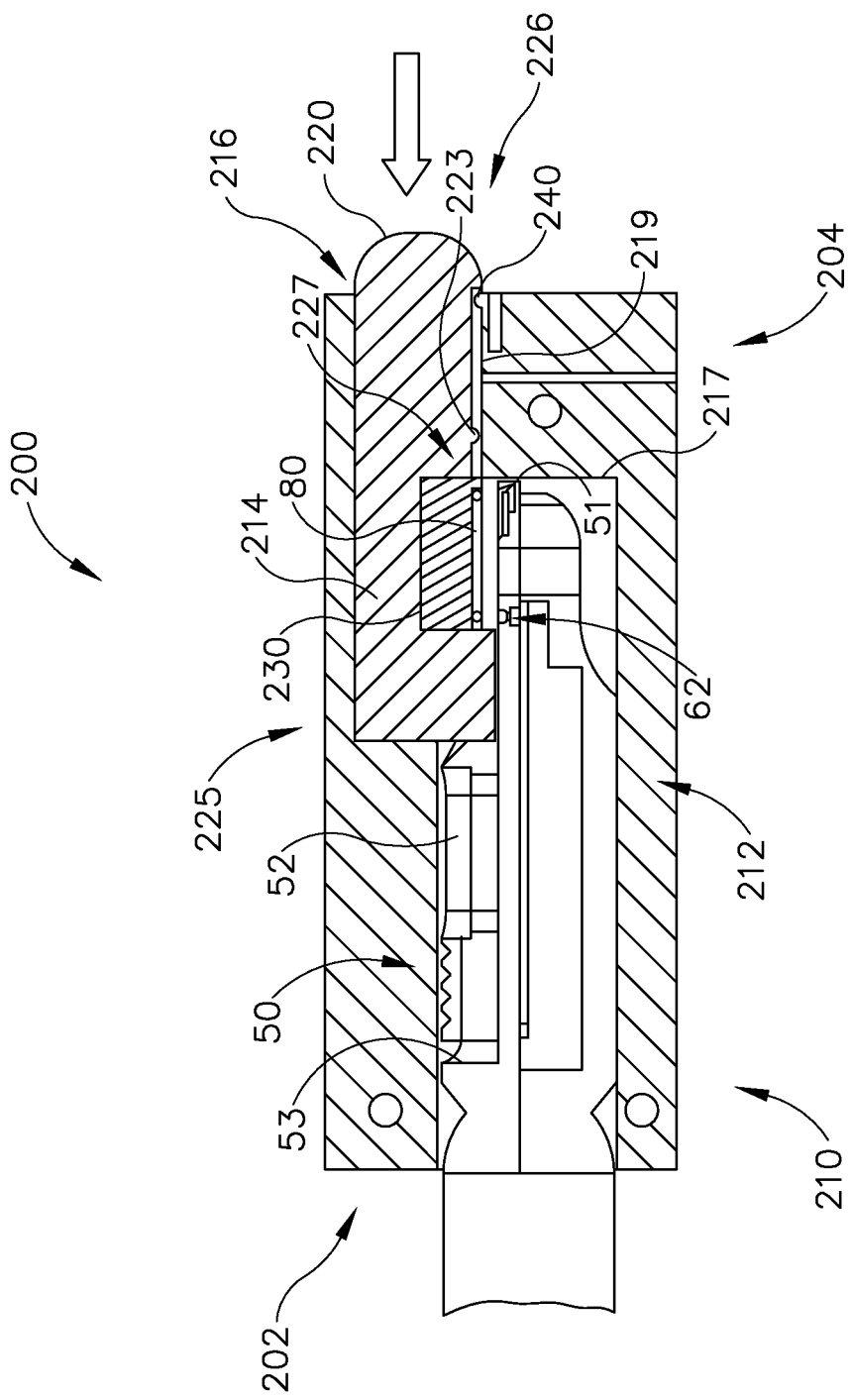
FIG. 12B depicts a side cross sectional view of a button of the needle loader of FIG. 10 being depressed within the needle loader of FIG. 10 and engaging a cover of the suturing instrument of FIG. 1.

In an exemplary use, needle loader (200) is used to insert needle (80) into curved channel (62) of end effector (50). As shown in FIG. 12A, end effector (50) of instrument (10) is inserted into first channel (212) along the longitudinal axis defined by first channel (212) until a distal end (51) of end effector (50) contacts a distal wall (217) of first channel (212) such that end effector (50) cannot be further inserted into first channel (212). End effector (50) is oriented such that cover (52) of end effector (50) is up. As shown in FIG. 12B, after end effector (50) has been fully inserted into channel first (212), the operator presses button (220) proximally within second channel (216) along a longitudinal axis defined by second channel (216). Proximal movement of button (220) within second channel (216) will cause plate (230) to move proximally within second channel (216) as well. Proximal movement of button (220) within second channel (216) will also cause engagement member (214) to contact cover (52) and begin to drive cover (52) in a proximal direction.

Figure 12C:
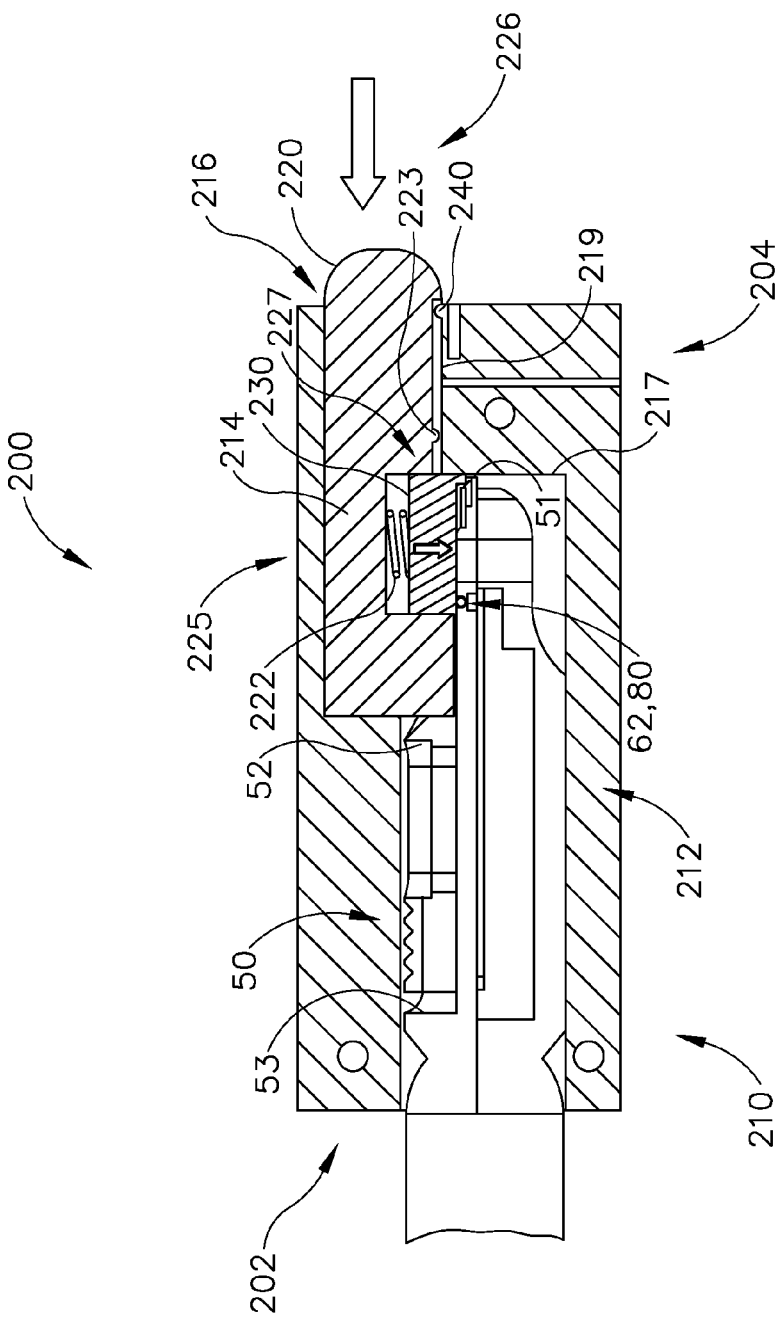
FIG. 12C depicts a side cross sectional view of the suturing instrument of FIG. 1 receiving a needle from a plate member of the needle loader of FIG. 10.
Figure 12D:
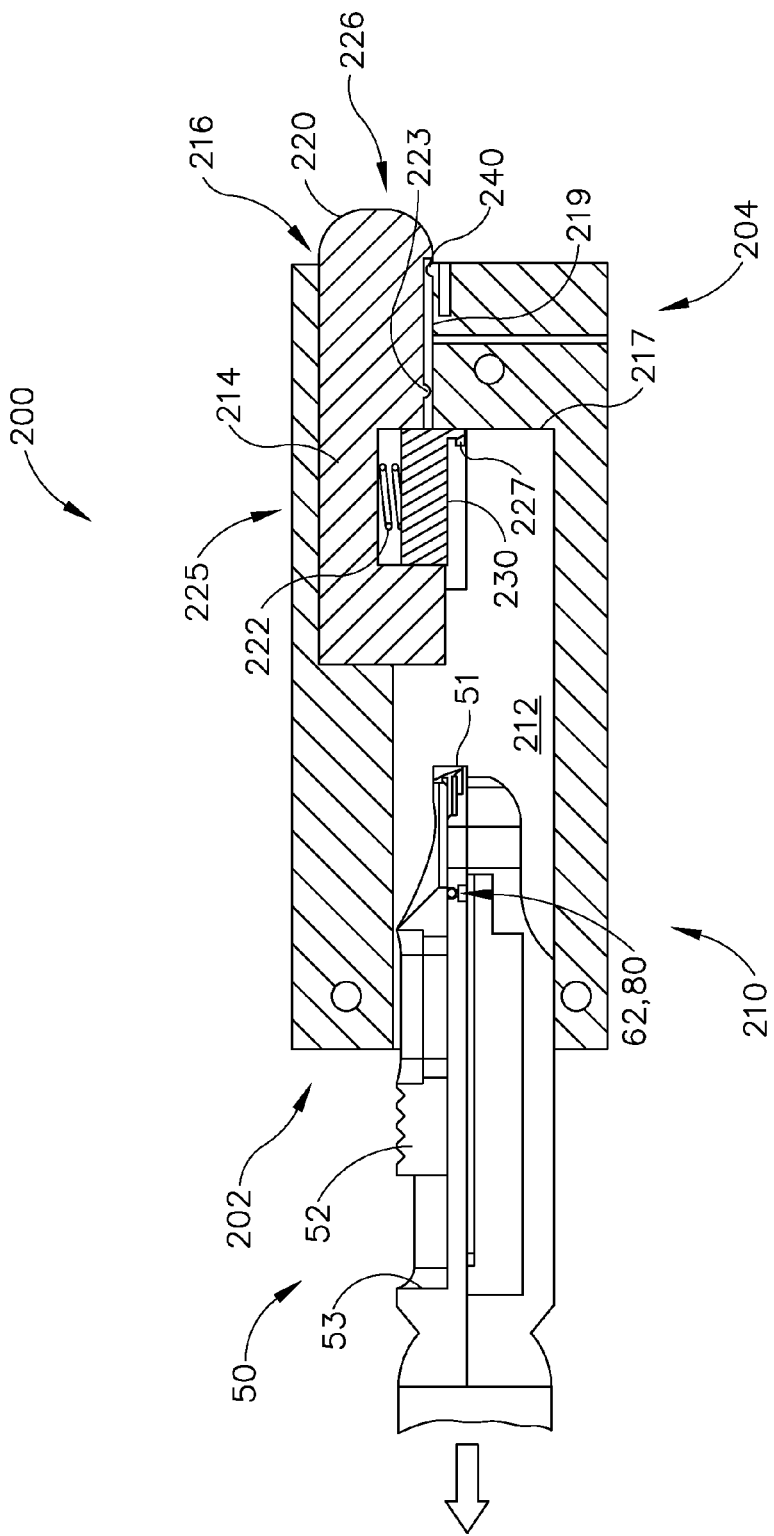
FIG. 12D depicts a side cross sectional view of the suturing instrument of FIG. 1 being removed from the needle loader of FIG. 10.

As shown in FIG. 12C, button (220) is driven into second channel (216) along the longitudinal axis defined by second channel (216) until a proximal end of cover (52) contacts a proximal wall (53) of end effector (50) such that cover (52), and subsequently button (220) cannot be further driven into second channel (216). At this point, cover (52) will have been driven to a proximal position by engagement member (214) such that curved channel (62) is exposed. It is also at this point that plate (230) will have moved to a proximal position such that plate (230) is no longer in contact with surface (219). Springs (222) will then drive plate (230) downwardly until the bottom of plate (230) contacts end effector (50) as shown in FIG. 12C. In this position, needle (80) will be encompassed by curved channel (62). While button (220) is still depressed and needle (80) is still within curved channel (62), end effector (50) is removed from channel (212) distally along the longitudinal axis defined by channel (212). The initial longitudinal movement of end effector (50) removes needle (80) from needle retainer (227) of button (220) such that needle (80) is no longer secured to button (220). As shown in FIG. 12D, as end effector (50) is further removed from channel (212), cover (52) returns to its original position because it is no longer being driven by engagement member (214).

Once end effector (50) is completely removed from needle loader (200), needle (80) should be oriented such that opening (83) of needle (80) aligns with gap (58) of end effector (50) as shown in FIG. 5. After this, instrument (10) is ready for use. It should be noted that needle loader (200) may further comprise suturing thread within body (210), such that the suturing thread is spooled about an internal or external portion of body (210). Such suturing thread may be already secured to needle (80), such that the operator will pull suturing thread from body (210) as the operator pulls the loaded end effector (50) away from body (210). However, body (210) need not comprise suturing thread. By way of example only, suturing thread may be provided as a separate component of needle loader (200).

C. Third Exemplary Button Actuated Needle Loader

Figure 13:
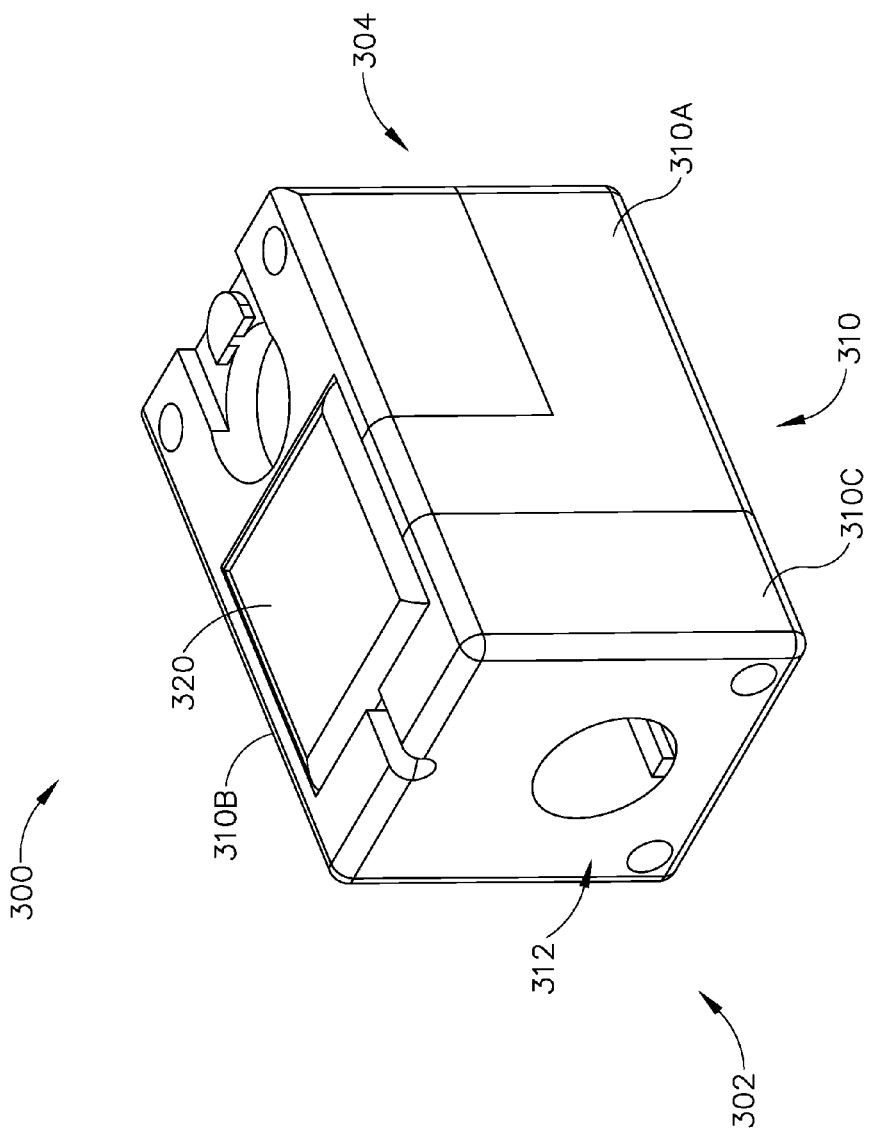
FIG. 13 depicts a perspective view of another exemplary alternative needle loader suitable for use with the instrument of FIG. 1.
Figure 14:
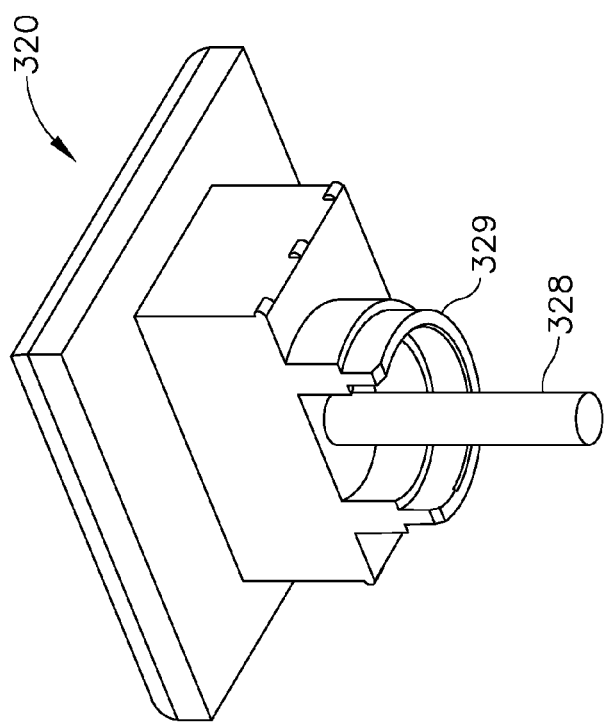
FIG. 14 depicts a perspective view of a button of the needle loader of FIG. 13.
Figure 15:
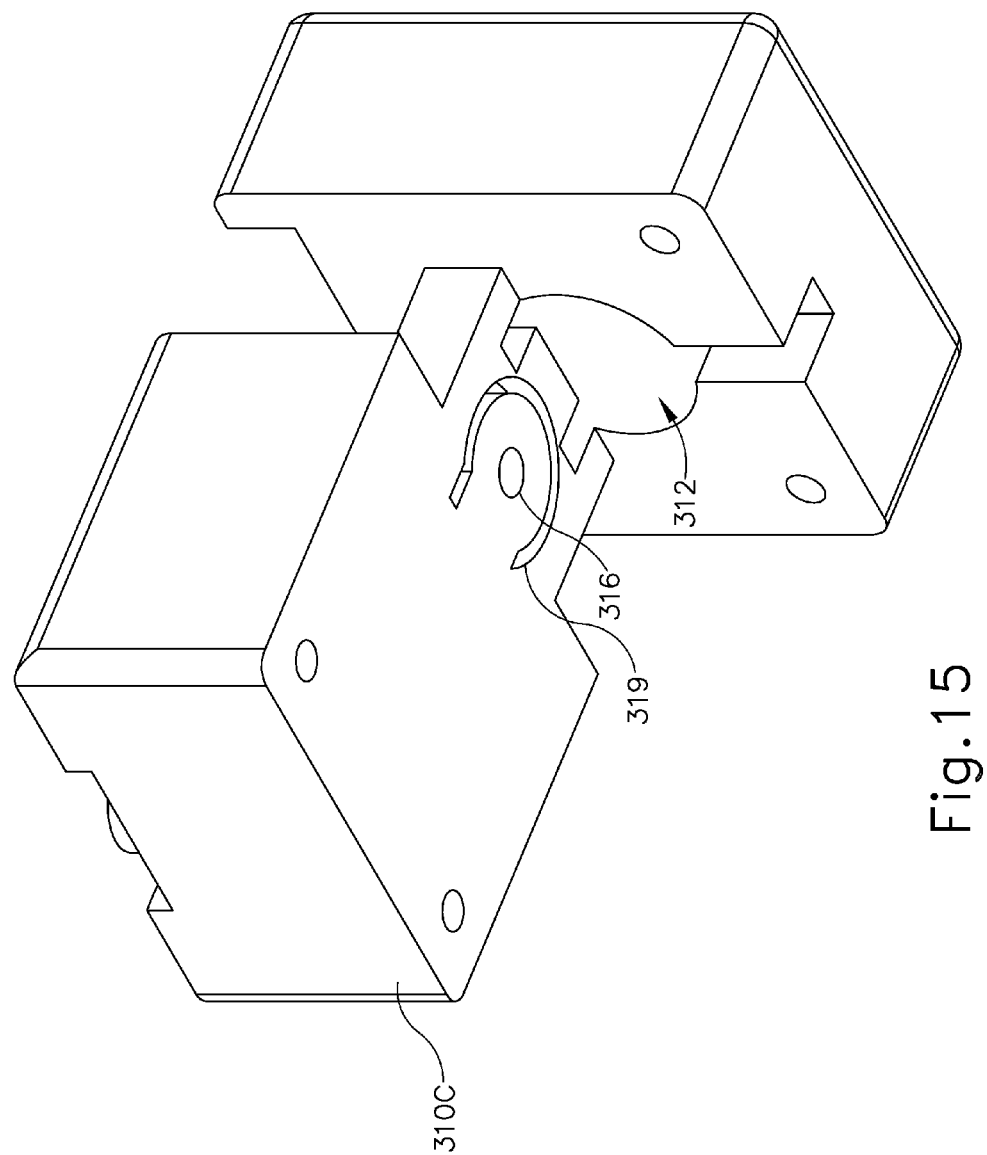
FIG. 15 depicts a perspective view of a center portion of a body of the needle loader of FIG. 13.
Figure 16:
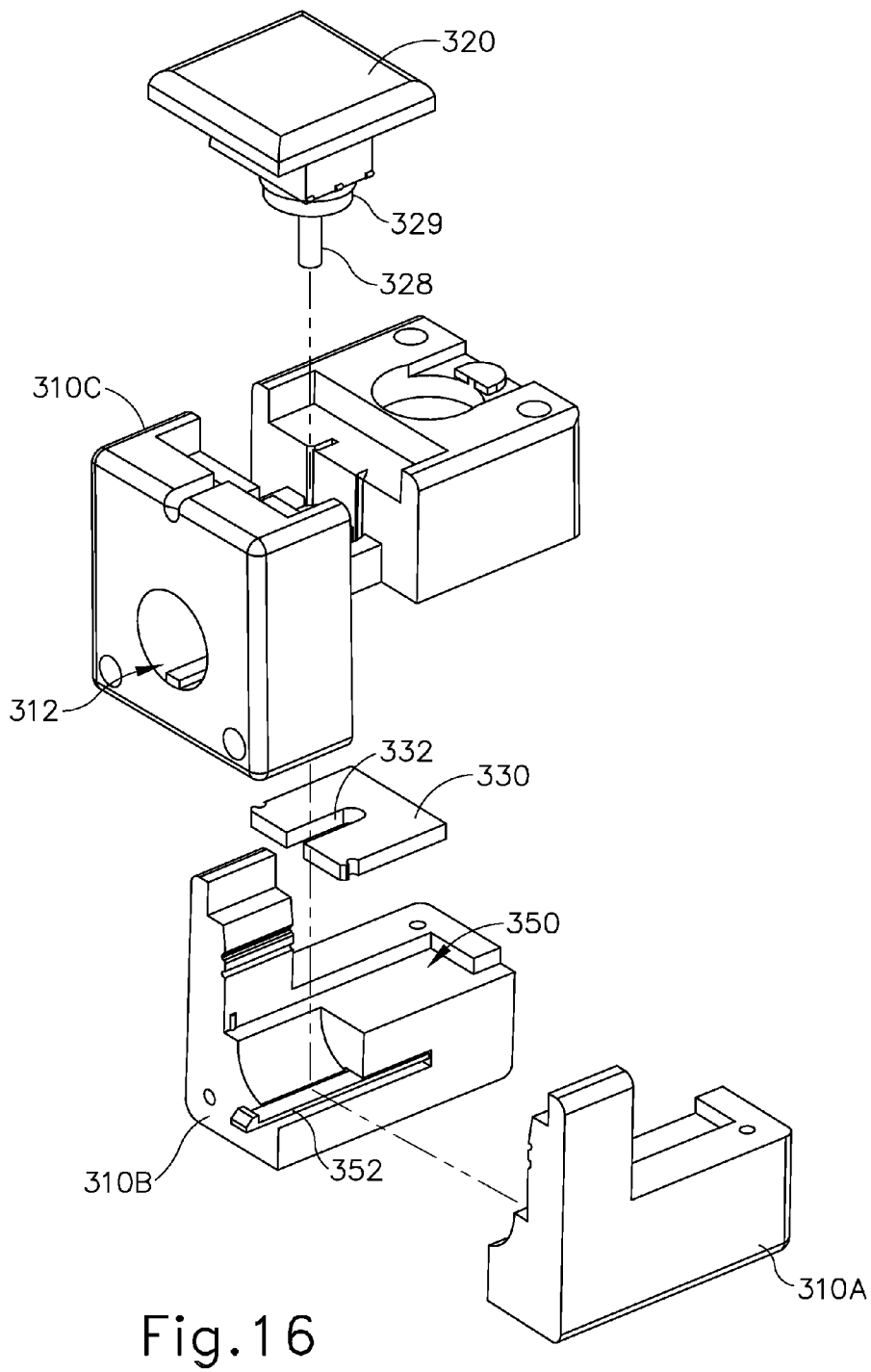
FIG. 16 depicts an exploded perspective view of the needle loader of FIG. 13.

FIG. 13 shows yet another exemplary alternative needle loader (300) that may be used to load a needle (80) in end effector (50). Needle loader (300) of this example comprises a body (310), a button (320), a plate (330), and needle (80). Body (310) comprises a first portion (310A), a second portion (310B), and a center portion (310C) which together define a first channel (312) and a second channel (350). First channel (312) is configured to receive end effector (50) of instrument (10). Second channel (350) is configured to receive plate (330). As best seen in FIGS. 14 and 16, button (320) comprises a stem (328). As best seen in FIG. 16, center portion (310C) of body (310) comprises an opening (316) configured to slidably receive stem (328). The underside of button (320) further comprises needle-shaped protrusion (329), the utility of which will be discussed in more detail below.

Center portion (310C) of body (310) comprises a needle-shaped opening (319) configured to slidably received needle-shaped protrusion (329). In the present example, needle (80) is slidably disposed within slot (319); however, in other versions of needle loader (300) needle may be releasably secured to the bottom of needle-shaped protrusion (329). By way of example only, the underside of needle-shaped protrusion (329) may be magnetized, may include needle retention tabs, may include needle retention crush ribs, etc. Various other suitable ways in which needle (80) may be releasably secured to the bottom of needle-shaped protrusion (329) will be apparent to those of ordinary skill in the art in view of the teachings herein.

Figure 17A:
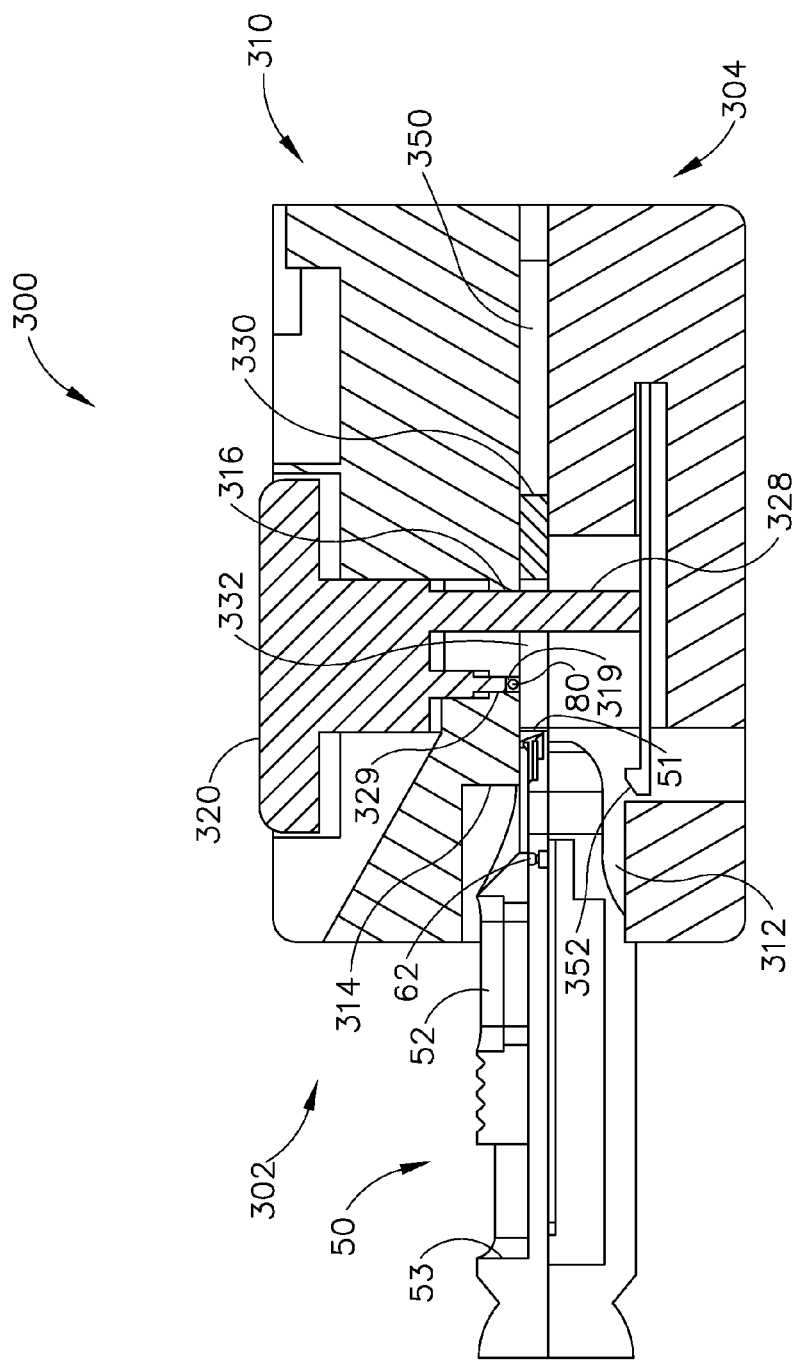
FIG. 17A depicts a side cross sectional view of the suturing instrument of FIG. 1 being inserted into the needle loader of FIG. 13 and engaging a plate member of the needle loader of FIG. 13.

Second portion (310B) of body (310) comprises a resilient tab (352). When assembled, stem (328) protrudes through opening (316) and the bottom of stem (328) rests upon tab (352). Tab (352) is configured to bend when force is exerted upon it in a downward direction. As seen in FIG. 16, plate (330) comprises a slot (332) that is configured to slidably extend around stem (328) of button (320). Plate (330) is configured to slide within second channel (350) along an axis defined by slot (332). As best seen in FIG. 17A, in an initial position, needle (80) rests upon the top of plate (330). Needle-shaped protrusion (329) rests on top of needle (80). It should therefore be understood that, in this initial position, button (320) is vertically supported by plate (330). Thus, a downward force upon button (320) in this initial position will not cause button (32) to move downwardly and will not cause tab (352) to bend.

Figure 17B:
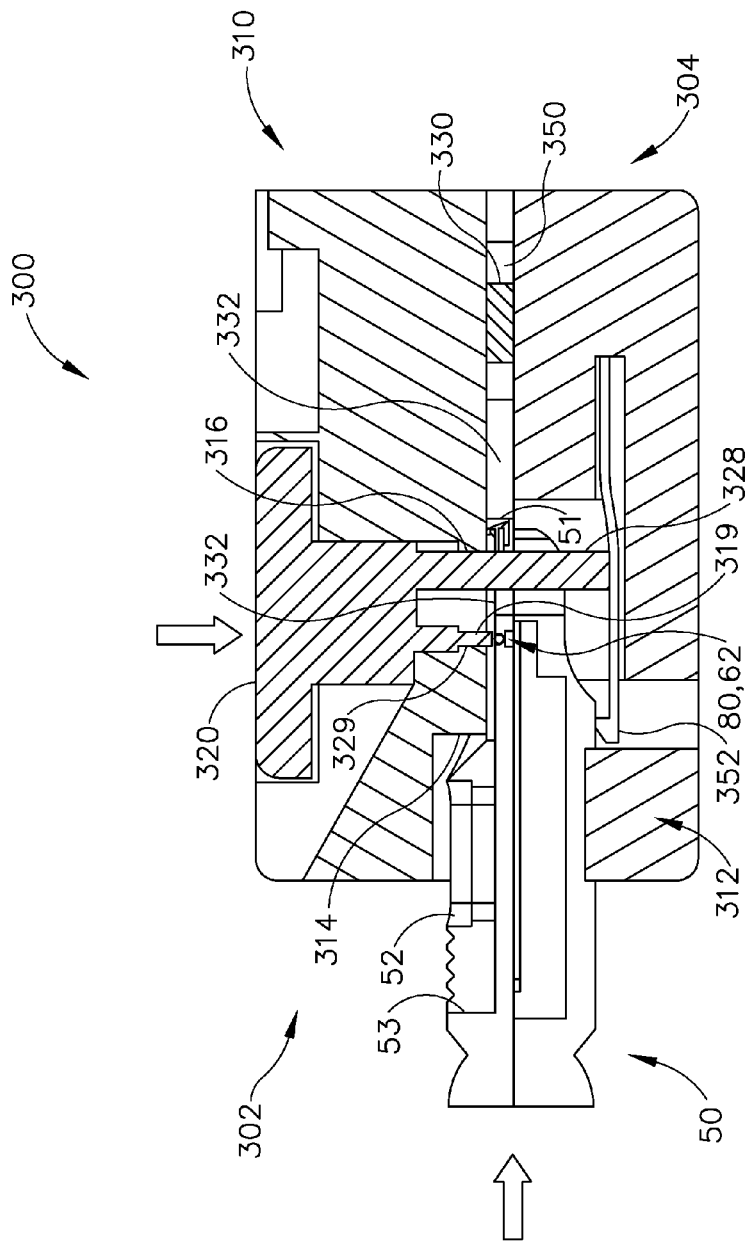
FIG. 17B depicts a side cross sectional view of a driving member of the needle loader of FIG. 13 engaging a cover of the suturing instrument of FIG. 1, the suturing instrument of FIG. 1 engaging a bendable tab of the needle loader of FIG. 13, and the suturing instrument of FIG. 1 receiving a needle from the needle loader of FIG. 13.

In an exemplary use, needle loader (300) is used to insert needle (80) into curved channel (62) of end effector (50). As shown in FIG. 17A, end effector (50) of instrument (10) is inserted into first channel (312) along the longitudinal axis defined by first channel (312) until a distal end (51) of end effector (50) contacts a proximal end of plate (330). End effector (50) is oriented such that cover (52) of end effector (50) is up. As shown in FIG. 17B, end effector (50) is further inserted into channel (312) along the longitudinal axis defined by channel (312). During the process of inserting end effector (50) into channel (312), a drive surface (314) contacts cover (52) and begins to drive cover (52) in a proximal direction. As shown in FIG. 17B, after contact between end effector (50) and drive surface (314), end effector (50) is further inserted into first channel (312) along the longitudinal axis defined by first channel (312) until the bottom of end effector (50) contacts a proximal end (353) of tab (352). Proximal end (353) of tab (352) is angled such that the distal movement of end effector (50) along the longitudinal axis defined by first channel (312) exerts a downward force upon tab (352) and tab (352) is bent downwardly. As shown in FIG. 17B, after contact between end effector (50) and tab (352), end effector (50) is further inserted into first channel (312) along the longitudinal axis defined by first channel (312) until a distal end (51) of end effector (50) contacts a distal wall (317) of first channel (312) such that end effector (50) cannot be further inserted into first channel (312). At this point, plate (330) will have been driven into a distal position within second channel (350), and tab (352) will have been forced into a downward position such that button (320) is no longer supported by either plate (330) or tab (352). Needle (80) slides along the top surface of plate (330) as plate (330) translates distally. As plate (330) reaches the distal position, needle-shaped opening (319) is eventually positioned under needle (80). Needle (80) may then pass downwardly through needle-shaped opening (319).

In some versions, needle (80) resides within needle-shaped opening (319) during the initial stage shown in FIG. 17A, such that needle (80) is not releasably secured to the bottom of needle-shaped protrusion (329). Needle (80) may thus slide distally with plate (330) during the transition from the positioning shown in FIG. 17A to the positioning shown in FIG. 17B. Various suitable ways in which needle (80) may be releasably held within needle-shaped opening (319) will be apparent to those of ordinary skill in the art in view of the teachings herein.

Figure 17C:
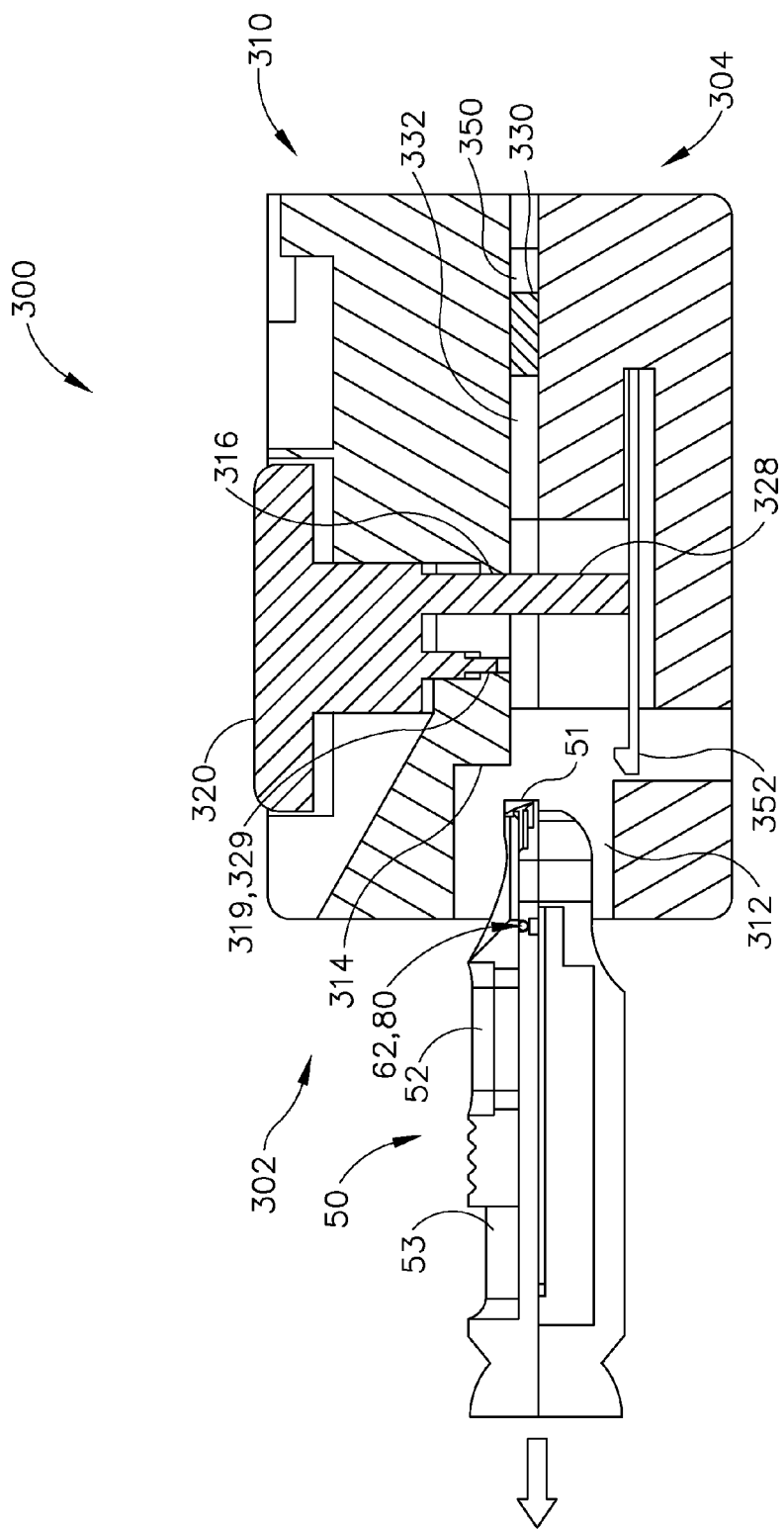
FIG. 17C depicts a side cross sectional view of the suturing instrument of FIG. 1 being removed from the needle loader of FIG. 13.

Once plate (330) has reached the distal position, the operator then presses button (320) downwardly such that needle-shaped protrusion (329) passes through needle-shaped opening (319) and urges needle (80) out of slot (319) and downwardly into curved channel (62) as shown in FIG. 17B. While button (320) is still depressed and needle (80) is still within curved channel (62), end effector (50) is removed from channel (312) distally along the longitudinal axis defined by channel (312). As shown in FIG. 17C, as end effector (50) is further removed from channel (312), cover (52) returns to its original position because it is no longer being driven by drive surface (314).

Once end effector (50) is completely removed from needle loader (300), needle (80) should be oriented such that opening (83) of needle (80) aligns with gap (58) of end effector (50) as shown in FIG. 5. After this, instrument (10) is ready for use. It should be noted that needle loader (300) may further comprise suturing thread within body (310), such that the suturing thread is spooled about an internal or external portion of body (310). Such suturing thread may be already secured to needle (80), such that the operator will pull suturing thread from body (310) as the operator pulls the loaded end effector (50) away from body (310). However, body (310) need not comprise suturing thread. By way of example only, suturing thread may be provided as a separate component of needle loader (300).

III. Miscellaneous

Any of the needle loaders (100, 200, 300) described herein may include one or more features that provide audible, visual, and/or tactile feedback indicating that a needle (80) has been successfully loaded in end effector (50). Various suitable forms that such feedback features may take will be apparent to those of ordinary skill in the art in view of the teachings herein. In addition, any of the needle loaders (100, 200, 300) described herein may include various poka-yoke features configured to ensure that end effector (50) is inserted into needle loader (100, 200, 300) at the appropriate orientation and depth, etc. Various suitable forms that such poka-yoke features may take will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

While terms such as "clockwise" and "counterclockwise" have been used to describe directions of rotational movement during exemplary uses of instruments, it should be understood that these specific rotational directions are being provided only in reference to the examples depicted in the drawings. It is contemplated that rotational movement may be provided in directions opposite to those used above. Therefore, use of the terms "clockwise" and "counterclockwise" in any examples described herein should not be viewed as limiting in any way.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. In addition or in the alternative, various teachings herein may be readily combined with various teachings in U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and/or U.S. Pat. No. 7,824,401, entitled "Surgical Tool With Writed Monopolar Electrosurgical End Effectors," issued Nov. 2, 2010, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a body defining a first channel extending along a first longitudinal axis and a second channel extending along a second longitudinal axis, wherein the first longitudinal axis is parallel to and offset from the second longitudinal axis, wherein the first channel and the second channel are in communication via a passageway extending transversely between the first channel and the second channel;
   (b) a drive member, wherein the drive member is configured to drive movement of a cover of a surgical instrument;
   (c) a button positioned within the second channel of the body and configured to move along the second longitudinal axis from a first position to a second position; and
   (d) a needle releasably secured within the second channel, wherein the button in the second position is configured to release the needle from the second channel thereby transversely directing the needle from the second channel to the first channel via the passageway for delivery into the surgical instrument.

2. The apparatus of claim 1, wherein the needle is a suture needle.

3. The apparatus of claim 1, wherein the apparatus further comprises suturing thread.

4. The apparatus of claim 3, wherein the suturing thread is disposed within the body.

5. The apparatus of claim 1, wherein the needle is removably attached to the button.

6. The apparatus of claim 1, wherein the first channel is configured to receive at least a portion of the surgical instrument along the first longitudinal axis.

7. The apparatus of claim 6, wherein the drive member is disposed within the first channel of the body.

8. The apparatus of claim 1, wherein the body further comprises an opening, wherein the button is slidably disposed within the opening.

9. The apparatus of claim 1, wherein the drive member is coupled to the button.

10. The apparatus of claim 1, wherein apparatus further comprises a plate member.

11. The apparatus of claim 10, wherein the plate member is configured to move in response to the button being depressed.

12. The apparatus of claim 11, wherein the needle is releasably secured to the plate member, wherein the plate member is configured to move and deliver the needle to the surgical instrument in response to the button being depressed.

13. An apparatus for delivering a needle to a surgical instrument, comprising:
   (a) a body defining a first channel extending along a first longitudinal axis and a second channel extending along a second longitudinal axis, wherein the first longitudinal axis is parallel to and offset from the second longitudinal axis, wherein the first channel and the second channel are in communication via a passageway extending transversely between the first channel and the second channel, wherein the first channel is configured to receive at least a portion of the surgical instrument along the first longitudinal axis;
   (b) a drive member positioned within the first channel of the body and configured to drive movement of a cover of a surgical instrument with the at least the portion of the surgical instrument received therein;
   (c) a button positioned within the second channel of the body and configured to move along the second longitudinal axis from a first position to a second position; and
   (d) a needle releasably secured within the second channel, wherein the button in the second position is configured to release the needle from the second channel thereby transversely directing the needle from the second channel to the first channel via the passageway for delivery into the surgical instrument.

14. The apparatus of claim 13, further comprising a plate resiliently received against the button within the second channel with the button in the first position, wherein the needle is releasably secured against the plate, wherein moving the button from the first position to the second position along the longitudinal axis thereby transversely directs the plate and the needle from the second channel toward the first channel for delivering the needle into the surgical instrument.

* * * * *